United States Patent
Yu et al.

(10) Patent No.: US 11,000,603 B2
(45) Date of Patent: May 11, 2021

(54) MULTI-SPECIFIC BINDING CONJUGATE, RELATED PHARMACEUTICAL COMPOSITIONS AND USE

(71) Applicant: Benhealth Biopharmaceutic (Shenzhen) Co., Ltd., Guangdong (CN)

(72) Inventors: Haoyang Yu, Guangdong (CN); Zhengcheng Li, Guangdong (CN); Jing Su, Guangdong (CN)

(73) Assignee: Benhealth Biopharmaceutic (Shenzhen) Co., Ltd., Guangdong (CN)

( * ) Notice: Subject to any disclaimer, the term of this patent is extended or adjusted under 35 U.S.C. 154(b) by 247 days.

(21) Appl. No.: 16/130,031

(22) Filed: Sep. 13, 2018

(65) Prior Publication Data

US 2018/0369411 A1 Dec. 27, 2018

Related U.S. Application Data

(63) Continuation of application No. PCT/CN2016/101984, filed on Oct. 13, 2016, and a
(Continued)

(30) Foreign Application Priority Data

Apr. 14, 2015 (CN) .......................... 201510175130.3
Apr. 29, 2016 (WO) ................ PCT/CN2016/080749

(51) Int. Cl.
*A61K 47/69* (2017.01)
*C07K 16/28* (2006.01)
(Continued)

(52) U.S. Cl.
CPC .......... *A61K 47/6937* (2017.08); *A61K 35/17* (2013.01); *A61K 39/3955* (2013.01);
(Continued)

(58) Field of Classification Search
None
See application file for complete search history.

(56) References Cited

U.S. PATENT DOCUMENTS

| 2004/0219203 | A1 | 11/2004 | Griffiths et al. |
| 2015/0010567 | A1 | 1/2015 | Bourquin et al. |
| 2015/0377869 | A1 | 12/2015 | Berkelman et al. |

FOREIGN PATENT DOCUMENTS

| CN | 104271602 A | 1/2015 |
| CN | 104829730 A | 8/2015 |

(Continued)

OTHER PUBLICATIONS

Dominguez et al., Vaccine 28 (2010) 1383-1390 (Year: 2010).*
(Continued)

*Primary Examiner* — Karl J Puttlitz
(74) *Attorney, Agent, or Firm* — Scully, Scott, Murphy & Presser, P.C.

(57) ABSTRACT

The present invention relates to a multi-specific binding conjugate, a related composition and use. The binding conjugate comprises binding moieties for two or more different receptors, co-receptors, antigens or cellular markers which moieties are coupled by a nanomaterial. The multi-specific binding conjugate can be used to modulate an immune response, treat or prevent a disease or condition (e.g., a cancer, autoimmune disease, pathogen infection or inflammatory disease).

9 Claims, 5 Drawing Sheets

Related U.S. Application Data continuation-in-part of application No. 15/548,630, filed as application No. PCT/CN2016/079307 on Apr. 14, 2016, now Pat. No. 10,758,625.

(51) Int. Cl.

| | |
|---|---|
| *A61K 35/17* | (2015.01) |
| *A61K 45/06* | (2006.01) |
| *A61K 39/395* | (2006.01) |
| *A61K 47/59* | (2017.01) |
| *A61P 35/00* | (2006.01) |
| *A61K 47/68* | (2017.01) |
| *C07K 16/30* | (2006.01) |
| *A61K 39/00* | (2006.01) |

(52) U.S. Cl.
CPC .......... *A61K 45/06* (2013.01); *A61K 47/593* (2017.08); *A61K 47/6849* (2017.08); *A61K 47/6851* (2017.08); *A61K 47/6935* (2017.08); *A61P 35/00* (2018.01); *C07K 16/2803* (2013.01); *C07K 16/283* (2013.01); *C07K 16/2809* (2013.01); *C07K 16/2887* (2013.01); *C07K 16/3092* (2013.01); *A61K 2039/505* (2013.01); *C07K 2317/31* (2013.01); *C07K 2317/73* (2013.01)

(56) References Cited

FOREIGN PATENT DOCUMENTS

| | | |
|---|---|---|
| WO | 03/048209 A1 | 6/2003 |
| WO | WO 2004/110390 A2 | 12/2004 |
| WO | WO 2005/103081 A2 | 11/2005 |
| WO | WO 2006/079120 A2 | 7/2006 |
| WO | WO 2006/094192 A2 | 9/2006 |
| WO | WO 2007/047609 A2 | 4/2007 |
| WO | WO 2013090293 A1 | 6/2013 |
| WO | WO 2014/079000 A1 | 5/2014 |
| WO | 2014/153002 A1 | 9/2014 |
| WO | 2016/165301 A1 | 10/2016 |
| WO | 2016/165302 A1 | 10/2016 |
| WO | 2016/165632 A1 | 10/2016 |
| WO | 2017/219974 A1 | 12/2017 |

OTHER PUBLICATIONS

Yu et al., Journal of Nanomaterials vol. 2015, Article ID 316968, 10 pages (Year: 2015).*
Karei Igaku Kenkyusho Zasshi (2000), 51(3-4), 111-120 (Year: 2000).*
Arruebo et al., Journal of Nanomaterials, vol. 2009, Article ID 439389, 24 pages, 2009 (Year: 2009).*
Zhi L. et al., "Cytotoxicity of Cytokine-Induced Killer Cells Targeted by the Bispecific Antibody Anti-CD3xanti-AFP on AFP Positive Hepatoma Cells", Chinese Journal of Biochemical Pharmaceutics, pp. 297-301 (May 31, 2010), together with an English-language abstract.
International Search Report dated Feb. 4, 2017 issued in PCT/CN2016/101984.
International Search Report dated Jul. 21, 2016 issued in PCT/CN2016/079307.
Li, Zhengcheng et al., "Production and function evaluation of a kind of bispecific antibody crosslinked with PLGA nanoparticles in vitro", Immunological Journal (Jan. 2016), vol. 32 No. 1, pp. 34-37, with English translation.
Glorius, P. et al., "The novel tribody [(CD20)2 x CD16] efficiently triggers effector cell-mediated lysis of malignant B cells", Leukemia, vol. 27, No. 1, pp. 190-201 (Jun. 4, 2012).
Kellner, C. et al., Heterodimeric bispecific antibody-derivatives against CD19 and CD16 induce effective antibody-dependent cellular cytotoxicity against B-lymphoid tumor cells, Cancer Letters, vol. 303, No. 2, pp. 128-139 (Apr. 28, 2011).
Schlenzka, J. et al., "Combined effect of recombinant CD19 x CD16 diabody and thalidomide in a preclinical model of human B cell lymphoma", Anti-Cancer Drugs, vol. 15, pp. 915-919 (Oct. 2014).
Extended Supplementary Partial European Search Report dated Nov. 26, 2019 received in European Patent Application No. 16 90 0170.8.
Tang, PhD J. et al., "Bispecific Antibodies, Nanoparticles and Cells: Bringing the Right Cells to Get the Job Done", Expert Opin Biol Ther. 15(9):1251-1255 (2015).
Prasad, S. et al., "Optimization of Stability, Encapsulation, Release, and Cross-Priming of Tumor Antigen-Containing PLGA Nanoparticles", Pharmaceutical Research, vol. 29, No. 9, 14, pp. 2565-2577 (Jul. 2012).
European Patent Office Communication dated Sep. 15, 2020 in corresponding European Patent Application No. 16 779 607.7.
Cheng K. et al., "Magnetic Antibody-Linked Nanomatchmakers for Therapeutic Cell Targeting", Nature Communications 5:4880 (Sep. 10, 2014).
Dominguez A L et al., "Targeting the Tumor Microenvironment With Anti-Neu/Anti-CD40 Conjugated Nanopartides for the Induction of Antitumor Immune Responses", Vaccine 28:1383-1390 (Feb. 3, 2010).
Katayose Y. et al., "MUC1-Specific Targeting Immunotherapy With Bispecific Antibodies: Inhibition of Xenografted Human Bile Duct Carcinoma Growth", Cancer Research 56:4205-4212 (Sep. 15, 1996).
Mahapatro A. et al., "Biodegradable Nanoparticles are Excellent Vehicle for Site Directed in-Vivo Delivery of Drugs and Vaccines", Journal of Nanobiotechnology 9(1):55 (Jan. 1, 2011).
Takemura S-I et al., "A Mutated Superantigen SEA D227A Fusion Diabody Specific to MUC1 and CD3 in Targeted Cancer Immunotherapy for Bile Duct Carcinoma", Cancer Immunol Immunother 51(1):33-44 (Mar. 1, 2002).
Yeheskely-Hayon D. et al., "Optically Induced Cell Fusion Using Bispecific Nanoparticles", Small 9 (22):3771-3777 (Nov. 25, 2013).
European Supplementary Partial Search Report dated Aug. 1, 2018 received in European Patent Application No. 16 77 9607.
Danielczyk, A. et al., "PankoMab: A Potent New Generation Anti-Tumour MUC1 Antibody", Cancer Immunol. Immunother., vol. 55, No. 11, pp. 1337-1347 (Nov. 2006).
Dong, B. et al., "A novel bispecific antibody, BiSS, with potent anticancer activities", Cancer Biology & Therapy, vol. 17, No. 4, pp. 364-370 (2016).
Fiedler, W. et al., "A phase I study of PankoMab-GEX, a humanised glyco-optimised monoclonal antibody to a novel tumour-specific MUC1 glycopeptide epitope in patients with advanced carcinomas", European Journal of Cancer, 63, pp. 55-63 (2016).
Kodama, H. et al., "Mutated SEA-D227A-conjugated antibodies greatly enhance antitumor activity against MUC1-expressing bile duct carcinoma", Cancer Immunother 50(10): 539-548 (2001).
Sadeqzadeh, E. et al., "Combined MUC1-Specific Nanobody-Tagged PEG-Polyethylenimine Polyplex Targeting and Transcriptional Targeting of tBid Transgene for Directed Killing of MUC1 Over-Expressing Tumour Cells", Journal of Controlled Release, vol. 156, No. 1, pp. 85-91 (Nov. 30, 2011).
Wei, X. et al., "Human MUC1 oncoprotein regulates p53-responsive gene transcription in the genotoxic stress response", Cancer Cell, vol. 7, pp. 167-178 (Feb. 2005).
Partial Supplementary European Search Report dated Aug. 13, 2018 in European Patent Application No. 16779607.7.
Extended Supplemental European Search Report dated Jan. 13, 2020 in European Application No. 17814712.0.
International Preliminary Report on Patentability dated Jul. 30, 2019 issued in International Application No. PCT/CN2018/073785.
International Search Report dated Sep. 26, 2017 issued in International Application No. PCT/CN2017/089307.
International Search Report dated Apr. 12, 2018 issued in International Application No. PCT/CN2018/073785.
Written Opinion dated Jul. 21, 2016 issued in International Application No. PCT/CN2016/079307.

(56) References Cited

OTHER PUBLICATIONS

Written Opinion dated Feb. 4, 2017 issued in International Application No. PCT/CN2016/101984.
Written Opinion dated Sep. 26, 2017 issued in International Application No. PCT/CN2017/089307.
Written Opinion dated Apr. 12, 2018 issued in International Application No. PCT/CN2018/073785.
European Office Action dated Feb. 5, 2021 received in European Application No. 16 900 170.8.

* cited by examiner

MULTI-SPECIFIC BINDING CONJUGATE, RELATED PHARMACEUTICAL COMPOSITIONS AND USE

CROSS-REFERENCE TO RELATED APPLICATIONS

This application is a continuation application of International Application No. PCT/CN2016/101984 filed Oct. 13, 2016, which claims priority to International Application No. PCT/CN2016/080749 filed Apr. 29, 2016. This application is also a continuation-in-part of U.S. Serial No. U.S. Ser. No. 15/548,630 filed Aug. 3, 2017, which is a 371 national phase of International Application No. PCT/CN2016/079307 filed Apr. 14, 2016 and claims priority to Chinese Application No. 201510175130.3 filed Apr. 14, 2015. The contents of each are all hereby incorporated by reference herein in their entirety.

TECHNICAL FIELD

The present invention directs to the field of medical immunology, and more particularly to a multi-specific binding conjugate for inducing an immune response to a disease such as a cancer or infectious disease. The invention also directs to a composition, method and use related to the conjugate.

BACKGROUND

Some antibody conjugates, such as multi-specific antibodies (such as bispecific antibodies), can bind to two or more different antigens. A number of recombinant strategies have been developed to synthesize a bispecific antibody, including a single-chain variable fragment (scFv)-derived form such as a diabody, a tandem diabody, BiTes (a bispecific T cell adaptor) and DART (double affinity re-targeting) as well as a form based on immunoglobulin G (IgG), such as Triomab, DVD-Ig (double variable domain antibody) and a two-in-one antibody. However, a bispecific antibody may have poor pharmacokinetic and physical properties (such as immunogenicity) as well as difficulty in manufacture. Therefore, improvement or alternative technique to such prior art is required.

SUMMARY OF INVENTION

A multispecific binding conjugate is disclosed herein. The multispecific binding conjugate described herein comprises binding moieties that bind to different receptors, co-receptors, antigens and/or cellular markers on different cells, and are coupled to a nanomaterial, such as a nanoparticle.

The multispecific binding conjugate disclosed herein comprises at least one first binding moiety and at least one second binding moiety coupled to a nanomaterial, such as a nanoparticle, wherein the first binding moiety binds to a receptor, co-receptor, antigen and/or cell marker on the cytotoxic effector cell, and the second binding moiety binds to a receptor, co-receptor, antigen and/or cellular marker on the target cell.

The cytotoxic effector cell can be a cytotoxic cell. The cytotoxic cell can be a leukocyte. The leukocyte may be selected from the group consisting of a macrophage, neutrophil, eosinophil, NK cell, B cell, and T cell. The leukocyte can be a NK cell. The leukocyte may be a NK-like T cell, i.e. NKT cell. The leukocyte may be a NK cell and T cell.

The target cell may be a cell to be cleared, and may be a diseased cell. For example, the target cell can be a cancer cell or a tumor cell. The target cell can be a leukemia cell. The target cell can be a lymphocyte. The target cell can be a metastatic cell. The target cell can be genetically modified. The target cell can contain gene mutation. The gene mutation can include oncogene mutation. The gene mutation can be mutation of a tumor-suppressing gene. The gene mutation can be mutation of the proto-oncogene. The target cell can be an inflammatory cell. The target cell can be an infected cell. The target cell can be a pathogenic cell.

The multispecific binding conjugate is preferably bispecific, wherein one binding site is directed to a receptor, co-receptor, antigen and/or cellular marker on a leukocyte, and the second binding site binds to a receptor, co-receptor, antigen and/or cellular marker on a target cell, which may be a cancer cell or tumor cell or pathogen (i.e., microorganism). The multispecific binding conjugate may also be trispecific, wherein one binding site (the first binding site) is directed to a receptor, co-receptor, antigen and/or cellular marker on a leukocyte, and the second binding site binds to a receptor, co-receptor, antigen and/or cellular marker on a target cell, which may be a cancer cell or tumor cell or pathogen (i.e., microorganism).

Exemplary receptor, co-receptor, antigen and/or cell marker on a T cell is selected from the group consisting of CD2, CD3, CD4, CD5, CD6, CD8, CD25, CD28, CD30, CD40, CD40L, CD44, CD45, CD69 and CD90. Exemplary receptor, co-receptor, antigen and/or cell marker expressed on a NK cell is selected from the group consisting of CD2, CD8, CD11b, CD16, CD38, CD56, CD57, ADAM17, KIR, KAR, KLR and CD137. Exemplary receptor, co-receptor, antigen and/or cell marker on a monocyte is selected from the group consisting of CD74, HLA-DR alpha chain, CD14, CD16, CD64 and CD89. Exemplary receptor, co-receptor, antigen and/or cell marker on a neutrophil is selected from the group consisting of CEACAM6, CEACAM8, CD16b, CD32a, CD89, CD177, CD11a, CD11b, and SLC44A2. The receptor, co-receptor, antigen and/or cell marker on a leukocyte may also be a checkpoint antigen, which may be selected from the group consisting of LSECtin, CTLA4, PD1, PD-L1, LAG3, B7-H3, B7-H4, KIR and TIM3. Preferably, the receptor, co-receptor, antigen and/or cellular marker on a T cell is CD3, CD4 or CD8, or the receptor, co-receptor, antigen and/or cellular marker on a NK cell is CD16 or CD56.

The second binding moiety can bind to a receptor, co-receptor, antigen and/or cellular marker on a diseased cell or pathogen. In certain embodiments, the second binding moiety of the conjugate can target a receptor, co-receptor, antigen, and/or cellular marker on any type of tumor and any type of tumor cell. Exemplary type of cancer that can be targeted includes acute lymphoblastic leukemia, acute myelogenous leukemia, biliary cancer, breast cancer, cervical cancer, chronic lymphocytic leukemia, chronic myelogenous leukemia, colorectal cancer, endometrial cancer, esophageal cancer, gastric cancer, head and neck cancer, Hodgkin's lymphoma, lung cancer, bone marrow thyroid cancer, non-Hodgkin's lymphoma, multiple myeloma, kidney cancer, ovarian cancer, pancreatic cancer, glioma, melanoma, liver cancer, prostate cancer, bladder cancer, neuroendocrine cancer, gastrointestinal pancreatic tumor, exocrine pancreatic cancer and Ewing sarcoma. However, a skilled artisan in the art will recognize that a known tumor-associated antigen is actually useful for any type of cancer.

The receptor, co-receptor, antigen and/or cell marker on a tumor cell or cancer cell can be selected from the group consisting of: carbonic anhydrase IX, alpha-fetoprotein, alpha-actinin-4, A3, A33 antibody-specific antigen, AFP, ART-4, B7, Ba 733, BAGE, BrE3-antigen, CA125, CAMEL, CAP-1, CASP-8/m, CCCL19, CCCL21, CD1, CD1a, CD2, CD3, CD4, CD5, CD8, CD11A, CD14, CD15, CD16, CD18, CD19, CD20, CD21, CD22, CD23, CD25, CD29, CD30, CD32b, CD33, CD37, CD38, CD40, CD40L, CD45, CD46, CD52, CD54, CD55, CD59, CD64, CD66a-e, CD67, CD70, CD70L, CD74, CD79a, CD79b, CD80, CD83, CD95, CD126, CD132, CD133, CD138, CD147, CD154, CDC27, CDK-4/m, CDKN2A, CXCR4, CXCR7, CXCL12, HIF-1alpha, colon-specific antigen-p (CSAp), CEA(CEACAM5), CEACAM6, c-met, DAM, EGFR, EGFRvIII, EGP-1, EGP-2, ELF2-M, Ep-CAM, Flt-1, Flt-3, folate receptor, G250 antigen, GAGE, gp100, GROB, HLA-DR, HM1.24, human chorionic gonadotropin (HCG) and its subunit, HER2/neu, HMGB-1, hypoxia-inducible factor (HIF-1), HSP70-2M, HST-2, Ia, IGF-1R, IFN-$\gamma$, IFN-$\alpha$, IFN-$\beta$, IL-2, IL-4R, IL-6R, IL-13R, IL-15R, IL-17R, IL-18R, IL-6, IL-8, IL-12, IL-15, IL-17, IL-18, IL-23, IL-25, insulin-like growth factor-1 (IGF-1), KC4-antigen, KS-1-antigen, KS1-4, Le-Y, LDR/FUT, macrophage migration inhibitory factor (MIF), MAGE, MAGE-3, MART-1, MART-2, NY-ESO-1, TRAG-3, mCRP, MCP-1, MIP-1A, MIP-1B, MIF, MUC1, MUC2, MUC3, MUC4, MUC5ac, MUC13, MUC16, MUM-1/2, MUM-3, NCA66, NCA95, NCA90, pancreatic cancer mucin, placental growth factor, p53, PLAGL2, prostate acid phosphatase, PSA, PRAME, PSMA, PlGF, ILGF, ILGF-1R, IL-6, IL-25, RS5, RANTES, T101, SAGE, S100, survivin, survivin-2B, TAC, TAG-72, tenascin, TRAIL receptor, TNF-alpha, Tn antigen, Thomson-Friedrich antigen, tumor necrosis antigen, TROP-2, VEGFR, ED-B fibronectin, WT-1, 17-1A-antigen, complement factor C3, C3a, C3b, C5a, C5, angiogenesis marker, bcl-2, bcl-6, Kras, cMET, oncogene product.

The receptor, co-receptor, antigen and/or cell marker on a tumor cell or cancer cell may also a cell surface protein selected from the group consisting of cholecystokinin B Receptor, gonadotropin releasing hormone receptor, somatostatin receptor 2, avb3 integrin, gastrin releasing peptide receptor, neurokinin 1 receptor, melanocortin 1 receptor, neurotensin receptor, neuropeptide Y receptor and C-type lectin-like molecule 1.

The pathogen may be selected from the group consisting of HIV virus, *Mycobacterium tuberculosis*, *Streptococcus agalactiae*, meticillin-resistant *Staphylococcus aureus*, *Legionella pneumophila*, *Streptococcus pyogenes*, *Escherichia coli*, *Neisseria gonorrhoeae*, *Neisseria meningitidis*, *Pneumococcus*, *Cryptococcus neoformans*, *Histoplasma capsulatum*, *Hemophilis influenzae B*, *Treponema pallidum*, Lyme disease spirochetes, *Pseudomonas aeruginosa*, *Mycobacterium leprae*, *Brucella abortus*, Rabies virus, Influenza virus, Cytomegalovirus, Type I herpes simplex virus, type II herpes simplex virus, human serum parvo-like virus, respiratory syncytial virus, varicella-zoster virus, hepatitis B virus, hepatitis C virus, measles virus, adenovirus, human T cell leukemia virus, Epstein-Barr virus, murine leukemia virus, mumps virus, vesicular stomatitis virus, Sindbis virus, lymphocyte choriomeningitis virus, Wart virus, Blue tongue virus, Sendai virus, Cat leukemia virus, Reovirus, Poliovirus, Simian virus 40, mouse mammary tumor virus, Dengue fever virus, rubella virus, West Nile virus, *Plasmodium falciparum*, *Plasmodium vivax*, *Toxoplasma gondii*, *Trypanosoma rangeli*, *Trypanosoma cruzi*, *Trypanosoma rhodesiensei*, *Trypanosoma brucei*, *Schistosoma mansoni*, *Schistosoma japonicum*, *Babesia bovis*, *Elmeria tenella*, *Onchocerca volvulus*, *Leishmania tropica*, *Trichinella spiralis*, *Theileria parva*, *Taenia hydatigena*, *Taenia ovis*, *Taenia saginata*, *Echinococcus granulosus*, *Mesocestoides corti*, *Mycoplasma arthritidis*, *M. hyorhinis*, *M. orale*, *M. arginini*, *Acholeplasma laidlawii*, *M. salivarium* and *M. pneumoniae*.

The first and/or second binding moiety may be selected from the group consisting of a small molecule, a cell targeting molecule, a ligand, a protein, a peptide, a peptoid, a DNA aptamer, a peptide nucleic acid, a vitamin, a substrate or a substrate analog, an antibody or a fragment thereof. The binding moiety is preferably a ligand, a receptor, an aptamer, an antibody or a fragment thereof, more preferably an antibody or a fragment thereof.

The antibody used may be a murine antibody, sheep antibody and so on, chimeric antibody, humanized and human antibody or a fragment thereof. The antibody may also be a heavy chain antibody (such as a camelid antibody) or a fragment thereof. The antibody may have various isotypes, preferably human IgG1, IgG2, IgG3 or IgG4, more preferably those comprising human IgG1 hinge and constant region sequences. The antibody or fragment thereof may be a chimeric human-mouse, humanized (human framework and murine hypervariable (CDR) region) or fully human antibody, and variant forms thereof, such as semi-IgG4 antibody (referred to as "single antibody"), as described by van der Neut Kolfschoten et al. (Science 2007; 317: 1554-1557). More preferably, the antibody or fragment thereof can be designed or selected to comprise a constant region sequence belonging to a particular allotype, which can reduce immunogenicity when administered to a human subject. The antibody or fragment thereof used may also be a multispecific antibody (e.g., a bispecific antibody) or a fragment thereof.

The nanomaterial may be a pharmaceutically acceptable nanomaterial, preferably a biodegradable nanomaterial, such as a nanoparticle. More preferably, the nanomaterial is any one of or a mixture of at least two of poly(lactic acid-co-glycolic acid), polylactic acid, polycaprolactone, polybutylene succinate, polyaniline, polycarbonate, poly(glycolide-co-lactide) or poly(glycolide-co-caprolactone), most preferably poly(lactic acid-co-glycolic acid) (PLGA), polylactic acid (PLA) and/or polycaprolactone (PCL). The average particle size of the nanoparticle may be, for example, about 10-990 nm, for example, about 900 nm, about 850 nm, about 800 nm, about 750 nm, about 700 nm, about 650 nm, about 600 nm, about 550 nm, about 500 nm, about 450 nm, about 400 nm, about 350 nm, about 300 nm, about 250 nm, about 200 nm, about 150 nm, about 100 nm or less, such as about 90 nm, about 80 nm, about 70 nm, about 60 nm, about 50 nm, about 40 nm, about 30 nm, about 20 nm, or about 10 nm. Preferably, the nanoparticle has an average particle size in the range of 10 to 500 nm, more preferably in the range of 10 to 300 nm.

The present disclosure also provides a pharmaceutical composition comprising the multispecific binding conjugate disclosed herein. The pharmaceutical composition may also comprise a leukocyte, preferably a NK cell, that binds to the multispecific binding conjugate. The pharmaceutical composition may also contain other therapeutic agent for treating the disease.

The present disclosure also provides a method of treating a disease or condition comprising administering the conjugate or pharmaceutical composition to a subject in need thereof.

The present disclosure also provides the use of the conjugate and pharmaceutical composition in the manufacture of a medicament for treating or preventing the disease or condition.

The present disclosure also relates to the conjugate and pharmaceutical composition for use in treating or preventing the disease or condition.

In certain embodiments, the conjugate and pharmaceutical composition disclosed herein can be used to treat cancer, such as the cancer disclosed herein. Exemplary type of cancer includes acute lymphoblastic leukemia, acute myelogenous leukemia, biliary cancer, breast cancer, cervical cancer, chronic lymphocytic leukemia, chronic myelogenous leukemia, colorectal cancer, endometrial cancer, esophageal cancer, gastric cancer, head and neck cancer, Hodgkin's lymphoma, lung cancer, bone marrow thyroid cancer, non-Hodgkin's lymphoma, multiple myeloma, kidney cancer, ovarian cancer, pancreatic cancer, glioma, melanoma, liver cancer, prostate cancer, bladder cancer, neuroendocrine cancer, gastrointestinal pancreatic tumor, exocrine pancreatic cancer and Ewing sarcoma. In other embodiments, a subject infected with a pathogenic organism such as a bacterium, virus, or fungus can be treated using the conjugate or pharmaceutical composition disclosed herein. Exemplary fungus that can be treated includes *Microsporum, Trichophyton, Epidermophyton, Sporothrix schenckii, Cryptococcus neoformans, Coccidioides immitis, Histoplasma capsulatum, Blastomyces dermatitidis* or *Candida albicans*. Exemplary virus includes human immunodeficiency virus (HIV), herpes virus, cytomegalovirus, rabies virus, influenza virus, human papilloma virus, hepatitis B virus, hepatitis C virus, Sendai virus, Cat leukemia virus, Reovirus, poliovirus, human serum parvo-like virus, Simian virus 40, respiratory syncytial virus, mouse mammary tumor virus, varicella-zoster virus, dengue virus, rubella virus, measles virus, adenovirus, human T cell leukemia virus, Epstein-Barr virus, murine leukemia virus, mumps virus, vesicular stomatitis virus, Sindbis virus, lymphocyte choriomeningitis virus or Blue tongue virus. Exemplary bacterium includes *Bacillus anthracis, Streptococcus agalactiae, Legionella pneumophila, Streptococcus pyogenes, Escherichia coli, Neisseria gonorrhoeae, Neisseria meningitidis, Pneumococcus, Hemophilis influenzae* B, *Treponema pallidum*, Lyme disease spirochetes, *Pseudomonas aeruginosa, Mycobacterium leprae, Brucella abortus, Mycobacterium tuberculosis* or *Mycoplasma*.

DESCRIPTION

Figure 1:
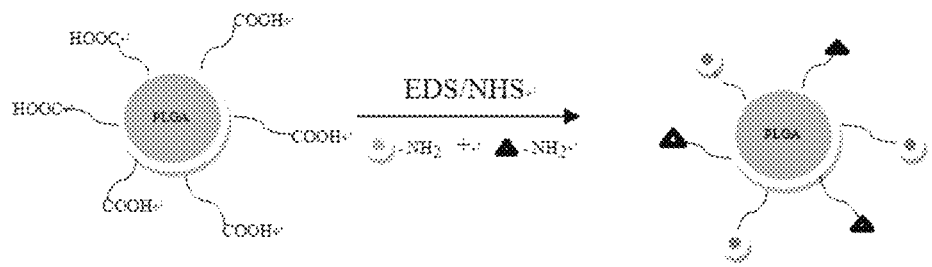
FIG. 1 is a schematic view showing the assembly of the bispecific antibody of Example 1.
Figure 2:
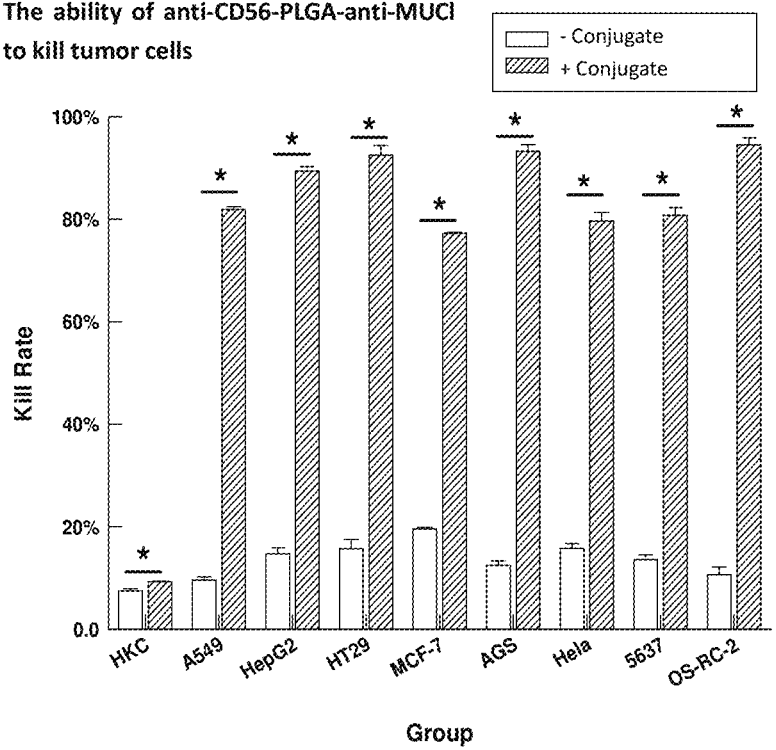
FIG. 2 shows the efficacy of the bispecific binding conjugate anti-CD56-PLGA-anti-MUC1 on killing cancer cells.
Figure 3:
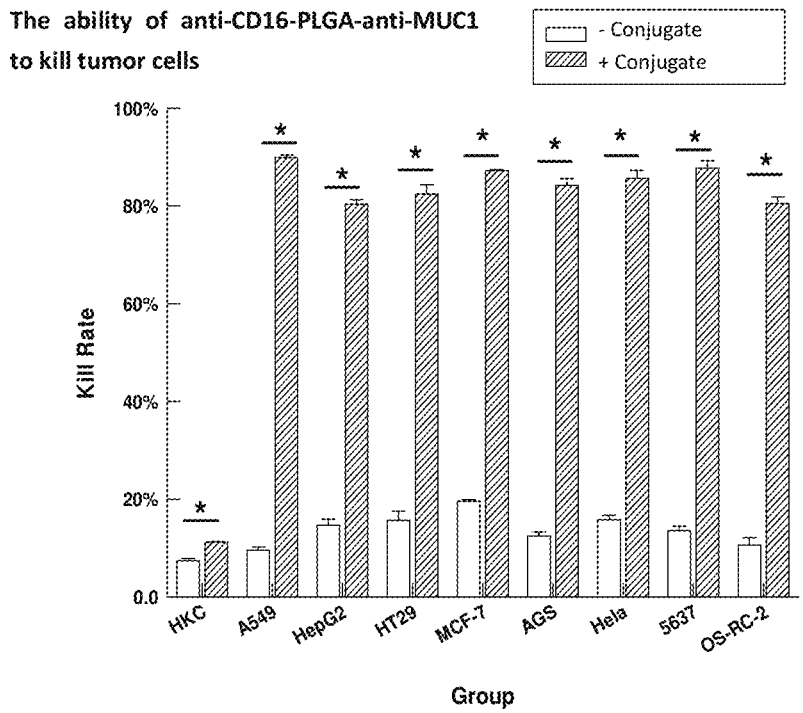
FIG. 3 shows the efficacy of the bispecific binding conjugate anti-CD16-PLGA-anti-MUC1 on killing cancer cells.
Figure 4:
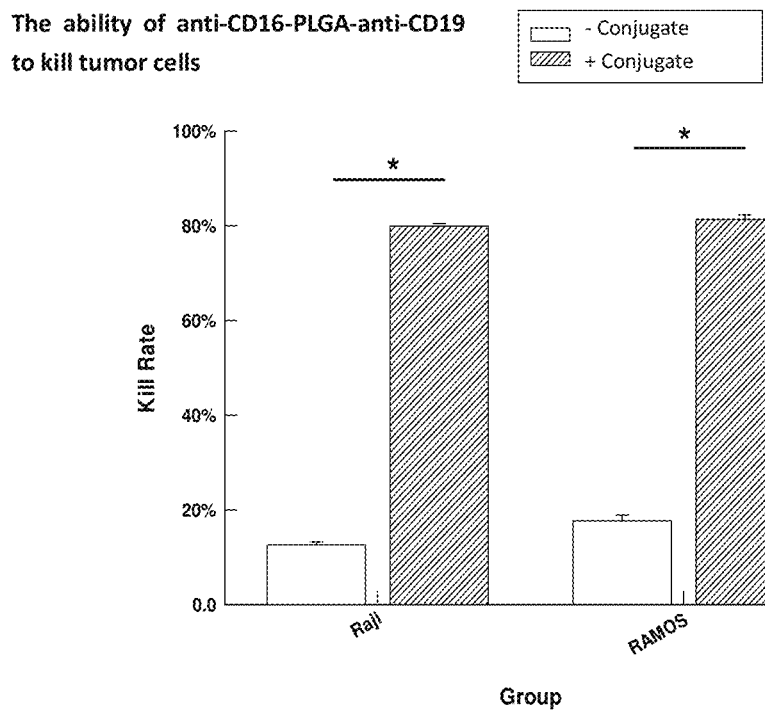
FIG. 4 shows the efficacy of the bispecific binding conjugate anti-CD16-PLGA-anti-CD19 on killing cancer cells.
Figure 5:
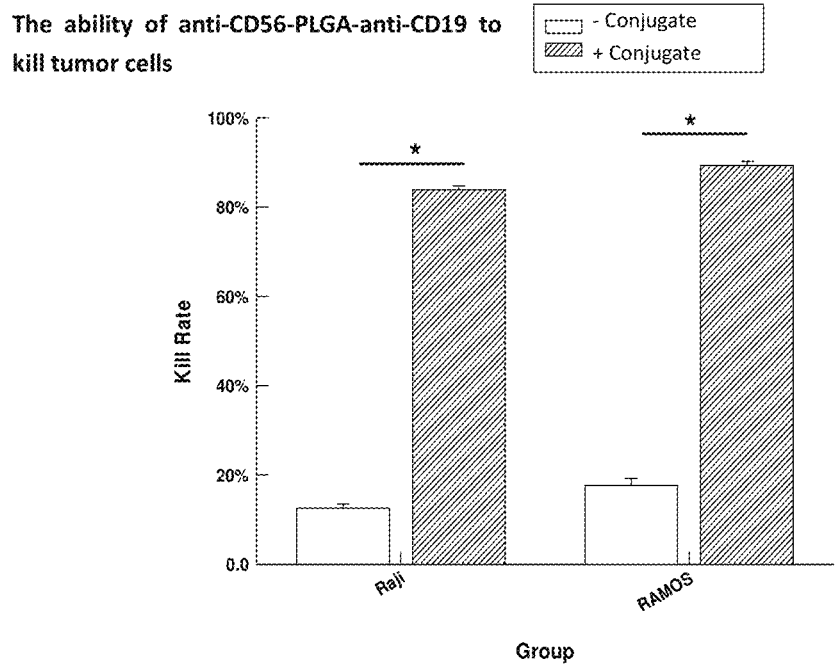
FIG. 5 shows the efficacy of the bispecific binding conjugate anti-CD56-PLGA-anti-CD19 on killing cancer cells.
Figure 6:
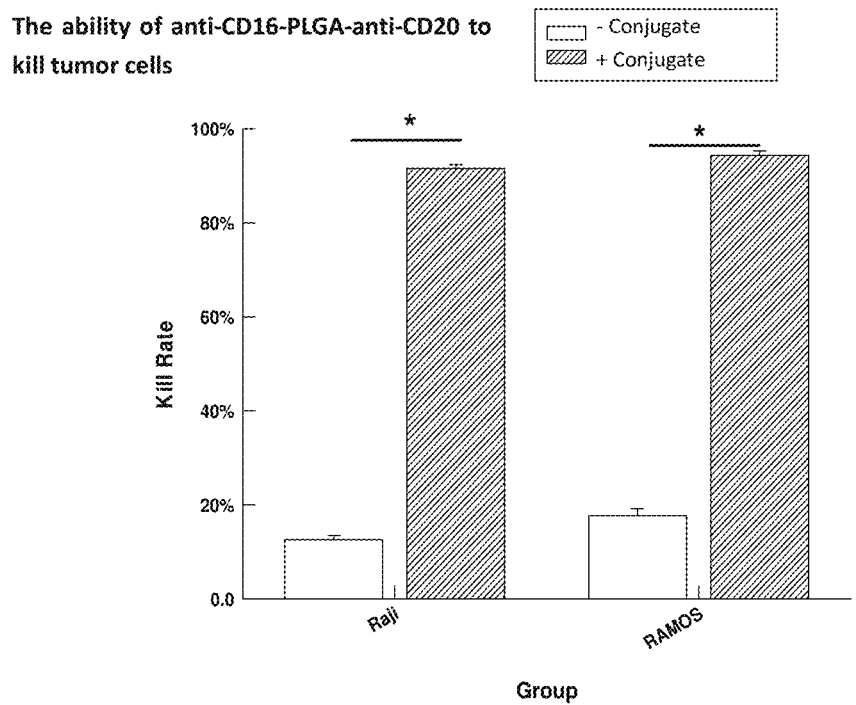
FIG. 6 shows the efficacy of the bispecific binding conjugate anti-CD16-PLGA-anti-CD20 on killing cancer cells.
Figure 7:
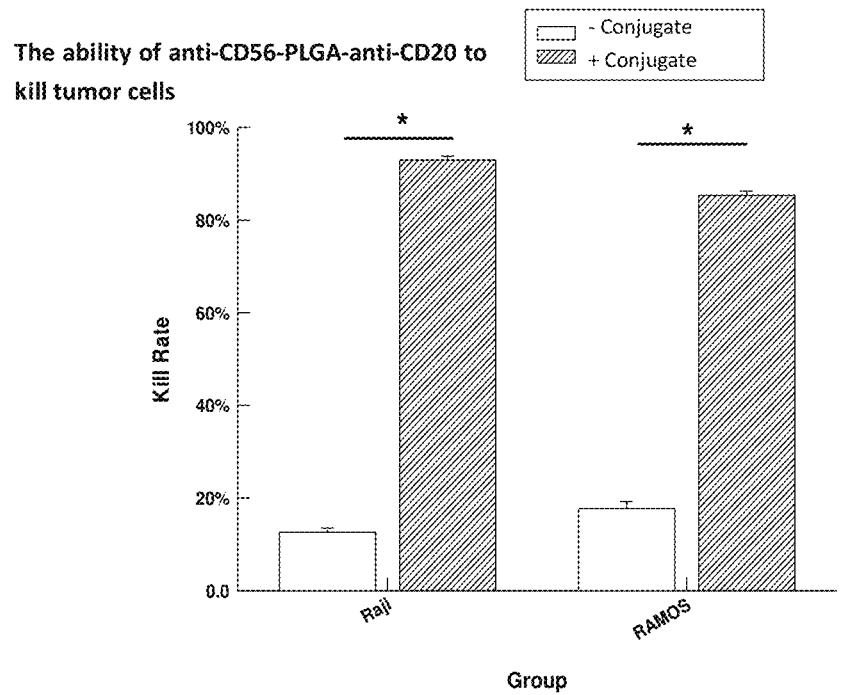
FIG. 7 shows the efficacy of the bispecific binding conjugate anti-CD56-PLGA-anti-CD20 on killing cancer cells.

Before the method and composition of the present invention are described, it should be understood that the invention is not limited to the specific method or composition described, and thus may, of course, vary. It should also be understood that the terms used herein are only illustrative, but not limiting. The description of the embodiments is provided for guiding a skilled artisan in the art to make and use the present invention, and is not intended to limit the scope of the invention, and also is not intended to indicate that the following experiments are all or only the experiments performed. Efforts have been made to ensure the accuracy of the number used (e.g., amount, temperature, etc.), but some experimental errors and deviations should be considered.

Unless defined otherwise, all technical and scientific terms used herein have the same meaning as commonly understood by a skilled artisan in the art. Although any method and material similar or equivalent to those described herein can be used in the practice or testing of the present invention, some potential and preferred methods and materials are now described. All publications mentioned herein are hereby incorporated by reference to disclose and describe the methods and/or materials related to the cited publications. It will be understood that in the event of a conflict, the present disclosure will control.

As will be apparent to a skilled artisan in the art upon reading this disclosure, each individual embodiment described and illustrated herein has discrete components and features that can be readily separated from or combined with the features in several other embodiments, without departing the scope or spirit of the invention. Any of the enumerated methods can be implemented in the order of the recited events or in any other order that is logically possible.

Unless stated otherwise, the article "a" or "an" as used in the description and in the appended claims means "one or more".

Where a range of values is provided, it should be understood that each intermediate value (up to one tenth of the lower limit unit) between the upper and lower limits of the range is also specifically disclosed, unless the context clearly dictates otherwise. The various smaller ranges between any such values or intermediate values within the range as well as other such values or intermediate values within the range are included in the invention. The upper and lower limits of these smaller ranges may be independently included in or excluded from the range and are subject to any particular exclusion in the range, wherein either or both or none of the upper and lower limits included in each range within the smaller range is also included in the present invention. Where the stated range includes one or both of the limits, the scope of the exclusion of either or both of such limits is also included in the invention.

A "therapeutic agent" is an atom, molecule or compound that can be used to treat a disease. An example of a therapeutic agent include an antibody, antibody fragment, peptide, drug, toxin, enzyme, nuclease, hormone, immunomodulator, antisense oligonucleotide, small interfering RNA (siRNA), chelating agent, boron compound, photosensitizer, dye and radioisotope.

As used herein, an "antibody" refers to a full-length (i.e., naturally occurring or formed by the process of rearrangement of a normal immunoglobulin gene segment) immunoglobulin molecule (e.g., an IgG antibody) or an immunoactive (i.e., specific binding) part of such immunoglobulin molecule (e.g., an antibody fragment). An "antibody" includes a monoclonal antibody, a polyclonal antibody, a bispecific antibody, a multispecific antibody, a murine antibody, a heavy chain antibody (such as a camelid antibody), a chimeric antibody, a humanized antibody and a human antibody, and the like. A "heavy chain antibody" is an antibody that contains only a heavy chain and does not contain a light chain, such as a camelid antibody, a cartilaginous fish (such as a shark) antibody, and the like.

An "antibody fragment" is a part of an intact antibody, such as F(ab')$_2$, F(ab)$_2$, Fab', Fab, Fv, scFv, dAb, and the like. Regardless of the structure, the antibody fragment binds to the same antigen as recognized by the full length antibody. For example, an antibody fragment comprises an isolated fragment consisting of variable regions, such as an "Fv" fragment consisting of a heavy or light chain variable region or a recombinant single-chain polypeptide molecule ("scFv protein") in which the light chain and heavy chain variable regions are joined by a peptide linker. A "single-chain antibody" is often abbreviated as "scFv" and consists of a polypeptide chain comprising $V_H$ and $V_L$ domains that interact with each other to form an antigen-binding site. The $V_H$ and $V_L$ domains are typically joined by a peptide having from 1 to 25 amino acid residues. An antibody fragment also includes a bifunctional antibody, a trifunctional antibody, and a single-domain antibody (dAb). An "antibody fragment" also includes a fragment of the heavy chain antibody, such as a single-domain antibody (sdAb) or a fragment comprising a variable region.

A "multispecific antibody" is an antibody that can simultaneously bind at least two targets with different structures (e.g., two different antigens, two different epitopes on the same antigen). A "bispecific antibody" is an antibody that can simultaneously bind to two targets with different structures.

If the amount administered is physiologically significant, the conjugate or composition described herein is described to be administered in a "therapeutically effective amount". It is physiologically significant if the presence of an agent produces a detectable change in the physiology of the subject. In a particular embodiment, if the presence of an antibody formulation causes an anti-cancer response or ameliorates a sign and symptom of an infectious disease state, it is physiologically significant. A physiologically significant effect may also be to elicit a humoral and/or cellular immune response in the subject, thereby causing growth inhibition or death of a target cell.

Multispecific (e.g., Bispecific) Binding Conjugate

A "multispecific binding conjugate" means that the conjugate can simultaneously bind to at least two targets with different structures (e.g., two different antigens, two different epitopes on the same antigen). A "bispecific binding conjugate" means that the conjugate can simultaneously bind to two targets with different structures.

Various embodiments are directed to a multispecific binding conjugate comprising a first binding moiety binding to a leukocyte and a second binding moiety binding to a receptor, co-receptor, antigen and/or cellular marker on a cell associated with a disease or a cell to be cleared, which moieties are coupled to a nanomaterial (such as a nanoparticle). The first binding moiety and/or the second binding moiety may have one or more binding specificities, for example, may be one or more monoclonal antibodies or fragments thereof, or a multispecific binding moiety, such as a bispecific antibody or fragment thereof.

Exemplary receptor, co-receptor, antigen and/or cell marker on a T cell includes CD2, CD3, CD4, CD5, CD6, CD8, CD25, CD28, CD30, CD40, CD40L, CD44, CD45, CD69 and CD90. For a NK cell, other exemplary receptor, co-receptor, antigen and/or cell marker can be selected from the group consisting of CD8, CD16, CD56, CD57, ADAM17 and CD137. For a monocyte, exemplary receptor, co-receptor, antigen and/or cell marker may be selected from the group consisting of CD74, HLA-DR alpha chain, CD14, CD16, CD64 and CD89; and for a neutrophil, exemplary receptor, co-receptor, antigen and/or cell marker includes CEACAM6, CEACAM8, CD16b, CD32a, CD89, CD177, CD11a, CD11b and SLC44A2. In a preferred embodiment, the first binding moiety for NK binds to CD16 or CD56. As discussed below, many examples of the disease-associated antigen, such as a tumor-associated antigen (TAA) or an antigen expressed by a pathogen, are known. Preferably, the TAA is MUC1, CD19, CD20, CD33, CD38, EGFR and HER2.

The binding moiety useful in the claimed conjugate is preferably an antibody or a fragment thereof. Techniques for preparing a monoclonal antibody that are actually directed against any target antigen are well known in the art. Known and/or commercially available antibodies can also be used. For example, an antibody that may be used is selected from the group consisting of hR1 (anti-IGF-1R), hPAM4 (anti-mucin), KC4 (anti-mucin), hA20 (anti-CD20), hA19 (anti-CD19), hIMMU31 (anti-AFP), hLL1 (anti-CD74), hLL2 (anti-CD22), R1-B4 (anti-CD22), hMu-9 (anti-CSAp), hL243 (anti-HLA-DR), hMN-14 (anti-CEACAM5), hMN-15 (anti-CEACAM6), hRS7 (anti-TROP-2), hMN-3 (anti-CEACAM6), CC49 (anti-TAG-72), J591 (anti-PSMA), D2/B (anti-PSMA), G250 (anti-carbonic anhydrase IX), infliximab (anti-TNF-α), certolizumab pegol (anti-TNF-α), adalimumab (anti-TNF-α), alemtuzumab (anti-CD52), bevacizumab (anti-VEGF), cetuximab (anti-EGFR), gemtuzumab (anti-CD33), ibritumomab (anti-CD20), panitumumab (anti-EGFR), rituximab (anti-CD20), tositumomab (anti-CD20), GA101 (anti-CD20), trastuzumab (anti-HER2/neu), tocilizumab (anti-IL-6 receptor), basiliximab (anti-CD25), daclizumab (anti-CD25), efalizumab (anti-CD11a), muromonab-CD3 (anti-CD3 receptor), natalizumab (anti-α4 integrin), BWA-3 (anti-histone H2A/H4), LG2-1 (anti-histone H3), MRA12 (anti-histone H1), PR1-1 (anti-histone H2B), LG11-2 (anti-histone H2B), LG2-2 (anti-histone H2B), P4/D10 (anti-gp120) and omalizumab (anti-IgE).

Exemplary antibody for the treatment of, for example, cancer includes, but are not limited to, LL1 (anti-CD74), LL2 or RFB4 (anti-CD22), veltuzumab (hA20, anti-CD20), rituximab (anti-CD20), obinutuzumab (GA101, anti-CD20), ranibizumab (anti-PD1), nivolumab (anti-PD1), MK-3475 (anti-PD1), AMP-224 (anti-PD1), pidilizumab (anti-PD1), MDX-1105 (anti-PD-L1), MEDI4736 (anti-PD-L1), MPDL3280A (anti-PD-L1), BMS-936559 (anti-PD-L1), Ipilimumab (anti-CTLA4), Trevizumab (anti-CTL4A), RS7 (anti-epithelium glycoprotein-1 (EGP-1, also known as TROP-2)), PAM4 or KC4 (both as anti-mucin), MN-14 (anti-carcinoembryonic antigen (CEA, also known as CD66e or CEACAM5)), MN-15 or MN-3 (anti-CEACAM6), Mu-9 (anti-colon specific antigen-p), Immu 31 (anti-alphafetoprotein), R1 (anti-IGF-1R), A19 (anti-CD19), TAG-72 (e.g. CC49), Tn, J591 or HuJ591 (anti-PSMA (prostate specific membrane antigen)), AB-PG1-XG1-026 (anti-PSMA dimer), D2/B (anti-PSMA), G250 (anti-carbonic anhydrase IX MAb), L243 (anti-HLA-DR), alemtuzumab (anti-CD52), bevacizumab (anti-VEGF), cetuximab (anti-EGFR), gemtuzumab (anti-CD33), ibritumomab (anti-CD20), panitumumab (anti-EGFR), tositumomab (anti-CD20), PAM4 (aka krivuzumab, anti-mucin), BWA-3 (anti-histone H2A/H4), LG2-1 (anti-histone H3), MRA12 (anti-histone H1), PR1-1 (anti-histone H2B), LG11-2 (anti-histone H2B), LG2-2 (anti-histone H2B) and trastuzumab (anti-ErbB2). These antibodies are known in the art.

In certain embodiments, the receptor, co-receptor, antigen and/or cellular marker on the target cell can be a cancer cell receptor or a cancer associated antigen, particularly selected from the group consisting of B cell line antigens (CD19, CD20, CD21, CD22, CD23, etc.), VEGF, VEGFR, EGFR, carcinoembryonic antigen (CEA), placental growth factor (PlGF), tenascin, HER-2/neu, EGP-1, EGP-2, CD25, CD30, CD33, CD38, CD40, CD45, CD52, CD74, CD80, CD138, NCA66, CEACAM1, CEACAM6 (carcinoembryonic antigen-associated cell adhesion molecule 6), MUC1, MUC2, MUC3, MUC4, MUC16, IL-6, alpha-fetoprotein (AFP), A3, CA125, colon-specific antigen-p (CSAp), folate receptor, HLA-DR, human chorionic gonadotropin (HCG), Ia, EL-2, insulin-like growth factor (IGF) and IGF receptor, KS-1, Le(y), MAGE, necrotic antigen, PAM-4, prostatic acid phosphatase (PAP), Pr1, prostate specific antigen (PSA), prostate specific membrane antigen (PSMA), S100, T101, TAC, TAG72, TRAIL receptor and carbonic anhydrase IX.

MUC1 antigen is highly abnormally expressed on the surface of the cell of many tumors (90% of solid cancers such as liver cancer, lung cancer, breast cancer, esophageal cancer, gastric cancer, colorectal cancer, cervical cancer, kidney cancer, bladder cancer, etc.), making it a potential target molecule for tumor-targeted therapy.

B cell expresses various cell surface molecules during their differentiation and proliferation. Examples include CD10, CD19, CD20, CD21, CD22, CD23, CD24, CD37, CD53, CD72, CD74, CD75, CD77, CD79a, CD79b, CD80, CD81, CD82, CD83, CD84, CD85 and CD86 leukocyte surface markers. These markers are generally considered to be therapeutic targets for the treatment of B cell disorders or diseases such as B cell malignancy, autoimmune disease, and transplant rejection. Antibodies that specifically bind to these markers have been developed, and some have been identified as therapeutic agents for the treatment of the diseases and disorders.

For multiple myeloma therapy, suitable targeting antibodies have been described for, e.g. CD38 and CD138 (Stevenson, Mol Med 2006; 12(11-12): 345-346; Tassone et al, Blood 2004; 104(12): 3688-96), CD74 (Stein et al, supra), CS1 (Tai et al, Blood 2008; 112(4): 1329-37) and CD40 (Tai et al, 2005; Cancer Res. 65(13):5898-5906).

CD74 antigen is highly expressed in B cell lymphoma (including multiple myeloma) and leukemia, certain T cell lymphoma, melanoma, colon cancer, lung and kidney cancer, glioblastoma and some other cancers (Ong et al, Immunology 98: 296-302 (1999)). A review of the use of CD74 antibody in treating cancer is provided in Stein et al, Clin Cancer Res. Sep. 15, 2007; 13 (18 Pt 2): 5556s-5563s, which is incorporated herein by reference. Preferred indications of an anti-CD74 antibody include, but are not limited to, non-Hodgkin's lymphoma, Hodgkin's disease, melanoma, lung cancer, renal cancer, colon cancer, glioblastoma multiforme, histiocytoma, myeloid leukemia and multiple myeloma.

In another preferred embodiment, an antibody against a pathogen can be used, and such an antibody is known. Commercially available antibodies against a variety of human pathogens (e.g., KPL, Inc., Gaithersburg, Md.) can be utilized, including antibodies against *Staphylococcus aureus* (Cat. No. 011-90-05), *Streptococcus agalactiae* (Cat. No. 011-90-08), *Streptococcus pyogenes* (Cat. No. 01-90-07), *Helicobacter pylori* (Cat. No. 01-93-94), *Borrelia burgdorferi* (Cat. No. 05-97-91), *Escherichia coli* (Cat. No. 01-95-91; 01-95-96), *Legionella* (Cat. No. 01-90-03), *Listeria* (Cat. No. 01-90-90), *Vibrio cholerae* (Cat. No. 01-90-50), *Shigella* (Cat. No. 16-90-01) and *Campylobacter* (Cat. No. 01-92-93).

In a preferred embodiment, the pathogen is selected from the group consisting of HIV virus, *Mycobacterium tuberculosis, Streptococcus agalactiae*, meticillin-resistant *Staphylococcus aureus, Legionella pneumophila, Streptococcus pyogenes, Escherichia coli, Neisseria gonorrhoeae, Neisseria meningitidis, Pneumococcus, Cryptococcus neoformans, Histoplasma capsulatum, Hemophilis influenzae B, Treponema pallidum*, Lyme disease spirochetes, *Pseudomonas aeruginosa, Mycobacterium leprae, Brucella abortus*, Rabies virus, Influenza virus, Cytomegalovirus, Type I herpes simplex virus, type II herpes simplex virus, human serum parvo-like virus, respiratory syncytial virus, varicella-zoster virus, hepatitis B virus, hepatitis C virus, measles virus, adenovirus, human T cell leukemia virus, Epstein-Barr virus, murine leukemia virus, mumps virus, vesicular stomatitis virus, Sindbis virus, lymphocyte choriomeningitis virus, Wart virus, Blue tongue virus, Sendai virus, Cat leukemia virus, Reovirus, Poliovirus, Simian virus 40, mouse mammary tumor virus, Dengue fever virus, rubella virus, West Nile virus, *Plasmodium falciparum, Plasmodium vivax, Toxoplasma gondii, Trypanosoma rangeli, Trypanosoma cruzi, Trypanosoma rhodesiensei, Trypanosoma brucei, Schistosoma mansoni, Schistosoma japonicum, Babesia bovis, Elmeria tenella, Onchocerca volvulus, Leishmania tropica, Trichinella spiralis, Theileria parva, Taenia hydatigena, Taenia ovis, Taenia saginata, Echinococcus granulosus, Mesocestoides corti, Mycoplasma arthritidis, M. hyorhinis, M. orale, M. arginini, Acholeplasma laidlawii, M salivarium* and *M. pneumoniae*, as disclosed in U.S. Pat. No. 6,440,416. The examples of this patent are incorporated herein by reference in their entirety.

Other antibodies that may be used include antibodies against infectious disease factors such as bacteria, viruses, mycoplasmas or other pathogens. Many antibodies against such infectious agents are known in the art, and any such known antibodies can be used in the claimed methods and compositions. For example, the following antibodies can be used: an antibody against the gp120 glycoprotein antigen of human immunodeficiency virus I (HIV-1); antibody against malaria parasites, such as monoclonal antibody against sporozoite (circumsporozoite antigen), antibody against schistosomulum surface antigen (Simpson et al, Parasitology, 83: 163-177, 1981; Smith et al, Parasitology, 84: 83-91, 1982; Gryzch et al, J. Immunol., 129: 2739-2743, 1982; Zodda et al, J. Immunol. 129: 2326-2328, 1982; Dissous et al, J. Immunol., 129: 2232-2234, 1982); antifungal antibody, such as anti-Sclerotinia scleroterum antibody (U.S. Pat. No. 7,910,702), anti-Glucose caprylic acid xylose mannan antibody (Zhong and Priofski, 1998, Clin Diag Lab Immunol 5: 58-64); anti-candida antibody (Matthews and Burnie, 2001, Curr Opin Investig Drugs 2: 472-76) and anti-sphingoglycolipid antibody (Toledo et al, 2010, BMC Microbiol 10:47).

Suitable antibodies have been developed for most of the microorganisms (bacteria, viruses, protists, fungi, other parasites) that cause infection in most people, and many have previously been used for in vitro diagnostic purposes.

These antibodies, as well as modified antibodies which can be produced by conventional methods, are suitable for use in the present invention.

The nanomaterial for coupling the first binding moiety (e.g., an antibody or a fragment thereof) and the second binding moiety (e.g., an antibody or a fragment thereof) may be a pharmaceutically acceptable nanomaterial, preferably a biodegradable nanomaterial, more preferably any one of or a mixture of at least two of poly(lactic acid-co-glycolic acid), polylactic acid, polycaprolactone, polybutylene succinate, poly aniline, polycarbonate, poly(glycolide-co-lactide) or poly(glycolide-co-caprolactone), most preferably poly(lactic acid-co-glycolic acid) (PLGA), polylactic acid (PLA) and/or polycaprolactone (PCL). These nanomaterials and methods for preparing them are known in the art, for example, the nanomaterials can be prepared using the methods described below.

Preparation of the Conjugate of the Invention

The method for preparing the multispecific binding conjugate of the present invention is described below by taking a bispecific binding conjugate comprising two antibodies coupled to a nanoparticle as an example. The preparation method comprises the following steps:

(1) preparing, collecting and activating the nanomaterial;
(2) connecting the nanomaterial obtained in step (1) with a mixture of the first antibody moiety and the second antibody moiety.

In the step (1), the preparation of the nanomaterial comprises: completely dissolving the nanomaterial with a solvent, stirring, adding water to form a uniform emulsion. The agitation may be carried out at a rotation speed of 500 to 20,000 rpm/min, for example, the rotation speed may be 500 rpm/min, 700 rpm/min, 800 rpm/min, 1000 rpm/min, 1100 rpm/min, 1200 rpm/min, 1300 rpm/min, 1400 rpm/min, 1480 rpm/min, 1500 rpm/min, 2000 rpm/min, 2200 rpm/min, 2500 rpm/min, 3000 rpm/min, 3500 rpm/min, 4000 rpm/min, 4200 rpm/min, 4500 rpm/min, 5000 rpm/min, 5500 rpm/min, 6000 rpm/min, 6500 rpm/min, 7000 rpm/min, 7500 rpm/min, 8000 rpm/min, 8500 rpm/min, 9000 rpm/min, 9500 rpm/min, 10000 rpm/min, 11000 rpm/min, 12000 rpm/min, 13000 rpm/min, 14000 rpm/min, 15000 rpm/min, 16000 rpm/min, 17000 rpm/min, 18000 rpm/min, 19000 rpm/min or 20000 rpm/min Higher speed can be used if necessary.

Preferably, the nanomaterial is any one of or a mixture of at least two of poly(lactic acid-co-glycolic acid) (PLGA), polylactic acid (PLA), polycaprolactone (PCL), polybutylene succinate, polyaniline, polycarbonate, poly(glycolide-co-lactide) or poly(glycolide-co-caprolactone).

Preferably, the solvent is any one of or a mixture of at least two of acetone, butanone, methanol, ethanol or isopropanol.

Preferably, the collection of the nanomaterial comprises: collecting the prepared nanomaterial by centrifugation, and then washing the nanomaterial by resuspending in deionized water twice. The centrifugation can be carried out at a rotation speed of 8000-15000 rpm/min, for example, the rotation speed can be 8000 rpm/min, 9000 rpm/min, 10000 rpm/min, 11000 rpm/min, 12000 rpm/min, 13000 rpm/min, 14000 rpm/min, 14500 rpm/min, 14800 rpm/min, 15000 rpm/min Higher speeds can be used if necessary. Nanomaterials (nanoparticles) can be collected or further purified by other methods. The nanoparticles may have an average particle size as described above.

Preferably, the activation of the nanomaterial comprises: activating the nanomaterial for 0.5 to 5 hours by using a mixed solvent of 1 to 10 mg/mL 1-ethyl-(3-dimethylaminopropyl)carbodiimide hydrochloride (EDS) and N-hydroxysuccinimide (NHS) at room temperature.

In the step (2) of the invention, the connection comprises: collecting the activated nanomaterial by centrifugation, and then washing the nanomaterial once with the connecting reaction solution, adding a mixture of the first antibody moiety and the second antibody moiety to be connected in an equal volume into the connecting reaction solution, and then resuspending the nanomaterial with the connecting reaction solution containing the first antibody moiety and the second antibody moiety and conducting the connecting reaction for 0.5 to 5 hours at room temperature. After the reaction, the nanomaterial is collected by centrifugation. The nanomaterial is washed twice in Dulbecco's phosphate buffer saline (D-PBS), and then resuspended in D-PBS and stored at 4° C. Other methods of activating the nanomaterial can be employed.

The method for preparing the multi-specific binding conjugate of the present invention specifically includes the following steps:

(1) preparing a nanomaterial: completely dissolving the nanomaterial in acetone at a concentration of 5 to 30 mg/mL, and adding the solution of the nanomaterial in acetone to the deionized water in 1:4 v/v of acetone and deionized water with magnetic stirring at 500 to 1500 rpm/min, to form a uniform emulsion, and then continuing to stir until the volatilization of acetone;

(2) collecting the nanomaterial: collecting the prepared nanomaterial by centrifugation at 8000 to 15000 rpm/min, and then resuspending in deionized water, which processes are repeated twice for washing the nanomaterial;

(3) activating the nanomaterial: activating the nanomaterial by using a mixed solvent of 1 to 10 mg/mL 1-ethyl-(3-dimethylaminopropyl)carbodiimide hydrochloride and N-hydroxysuccinimide at room temperature for 0.5 to 5 hours;

(4) connecting the nanomaterial with antibodies: collecting the activated nanomaterial by centrifugation, and then washing the nanomaterial once with 0.1 M D-PBS at pH=8.0, and adding a mixture of the first antibody moiety and the second antibody moiety to be connected in an equal volume into the connecting reaction solution, and then resuspending the nanomaterial with the connecting reaction solution containing the first antibody moiety and the second antibody moiety and conducting the connecting reaction for 0.5 to 5 hours at room temperature. After the reaction, the nanomaterial is collected by centrifugation. The nanomaterial is washed twice in D-PBS, and then resuspended in D-PBS and stored at 4° C.

Pharmaceutical Composition

The invention also relates to a pharmaceutical composition comprising the multispecific binding conjugate. The pharmaceutical composition may also comprise a leukocyte, such as T cell, NK cell.

The pharmaceutical composition herein may be formulated using one or more physiologically acceptable carriers comprising excipients and auxiliaries which facilitate the entry of the active agent into the pharmaceutically acceptable formulation. Proper formulation depends on the route of administration chosen. For example, an overview of pharmaceutical composition can be found, for example, in Ansel et al, PHARMACEUTICAL DOSAGE FORMS AND DRUG DELIVERY SYSTEMS, 5th edition (Lea & Febiger 1990); and Gennaro (ed.), REMINGTON'S PHARMACEUTICAL SCIENCES, 18th edition (Mack Publishing Company 1990) and its revised edition. The pharmaceutical composition disclosed herein may further comprise one or more diluents, excipients or carriers that are pharmaceutically acceptable. The pharmaceutical composition may comprise a drug or pharmaceutical agent, a carrier, an adjuvant such as a preservative, a stabilizer, a wetting or emulsifying agent, a dissolution promoter, a salt for regulating the osmotic pressure, and/or a buffer.

In addition, the pharmaceutical composition may also contain other therapeutically valuable substances, such as one or more other therapeutic agents for treating the disease. For example, other therapeutic agents may be other agents for treating cancer, such as cyclophosphamide, etoposide, carmustine, vincristine, etc., and may also be antibodies used to treat cancers, antibody-drug conjugates (ADC), interferons and/or checkpoint inhibitor antibodies.

Therapeutic Treatment

Various embodiments are directed to methods of treating a disease or condition (e.g., cancer) in a subject, such as a mammal, including a human, domesticated or companion animals, such as a dog and a cat, comprising administering to the subject a therapeutically effective amount of the conjugate or pharmaceutical composition described herein.

The conjugate or pharmaceutical composition described herein may be formulated to be administered subcutaneously or even by other parenteral routes, such as intravenously, intramuscularly, intraperitoneally or intravascularly, to a mammal via, for example, bolus injection or continuous infusion for intravenous administration. Preferably, the conjugate or pharmaceutical composition is infused for a period of less than about 4 hours, and more preferably for a period of less than about 3 hours. For example, the first bolus can be infused over 30 minutes, preferably even 15 minutes, and the remainder is infused over the next 2 to 3 hours. The injectable preparation may be provided in unit dosage form, for example, in ampoules or in multi-dose containers, with a preservative added. The composition may take such forms as a suspension, solution or emulsion in oily or aqueous vehicle, and may contain a formulating agent such as suspending, stabilizing and/or dispersing agents. Alternatively, the active ingredient may be in the form of a powder which is reconstituted with a suitable vehicle, such as sterile pyrogen-free water, before use.

Additional pharmaceutical methods can be employed to control the duration of action of the therapeutic conjugate, pharmaceutical composition, and/or other therapeutic agents. Controlled release formulation can be prepared by using a polymer to complex or adsorb the agent to be administered. For example, a biocompatible polymer includes poly(ethylene-vinyl acetate) copolymer matrix and polyanhydride copolymer matrix of stearic acid dimers and sebacic acid. Sherwood et al, Bio/Technology 10: 1446 (1992). The rate of release from such a matrix depends on the molecular weight of the therapeutic agent, the amount of agent within the matrix, and the size of the dispersed particles. Saltzman et al, Biophys. J. 55: 163 (1989); Sherwood et al., supra. Other solid dosage forms are described in Ansel et al, PHARMACEUTICAL DOSAGE FORMS AND DRUG DELIVERY SYSTEMS, 5th edition (Lea & Febiger 1990); and Gennaro (ed.), REMINGTON'S PHARMACEUTICAL SCIENCES, 18th edition (Mack Publishing Company 1990) and its revised version.

More generally, the dosage of the conjugate administered to a human will vary depending on factors such as the age, weight, height, sex, general medical condition, and past medical history of the patient. It may be desirable to provide the recipient with a conjugate dose as a single intravenous infusion in the range of about 0.1 µg/kg to 25 mg/kg, by total amount of the first binding moiety and the second binding moiety in the multispecific binding conjugate, but lower or higher doses can also be administered, as the case may be. For example, for a 70 kg patient, a dose of 0.1 µg/kg-20 mg/kg is 0.7 µg-1400 mg. The dose can be repeated as needed, for example, once a week for 4 to 10 weeks, once a week for 8 weeks or once a week for 4 weeks. In maintenance therapy, it can also be administered at a lower frequency, if desired, such as every other week for several months, or monthly or quarterly for many months. It is also possible to administer 2, 3, 4, 5 or 6 times continuously for each course of treatment, for example, at an interval of about 10 days, 15 days, 20 days, 25 days, 30 days, 35 days, 40 days, 45 days, 50, 55 days or 60 days or more after continuous administration for the next course of treatment.

The conjugate can be administered with an effector cell such as leukocyte (such as T cell, NK cell), for example, via intravenous reinfusion. When the conjugate is administered with the effector cell, for example, it is performed once a week for 4-10 weeks, once weekly for 8 weeks or once weekly for 4 weeks. In maintenance therapy, the conjugate and effector cell can also be administered at a lower frequency if desired, such as every other week or weeks, for several months, or monthly or quarterly for many months. It is also possible to administer 2, 3, 4, 5 or 6 times continuously for each course of treatment, for example, at an interval of about 10 days, 15 days, 20 days, 25 days, 30 days, 35 days, 40 days, 45 days, 50, 55 days or 60 days or more after continuous administration for the next course of treatment.

In general, the dosage of other therapeutic agents for human administration will vary depending on factors such as the age, weight, height, sex, general medical condition, and past medical history of the patient. It may be desirable to provide the recipient with a conjugate dose as a single intravenous infusion in the range of about 1 mg/kg to 25 mg/kg, but lower or higher doses may also be administered, as appropriate. For example, for a 70 kg patient, the dose of 1-20 mg/kg is 70-1,400 mg. The dose can be repeated as needed, for example, once a week for 4-10 weeks, once a week for 8 weeks or once a week for 4 weeks. In maintenance therapy, it can also be administered at a lower frequency, if desired, such as every other week for several months, or monthly or quarterly for many months.

Other therapeutic agents can be administered in one dose every 2 weeks or 3 weeks, for a total of at least 3 doses repeated. Alternatively, the combination can be administered twice a week for 4 to 6 weeks. If the dose is reduced to approximately 200-300 mg/m$^2$ (340 mg per dose for 1.7 m patients or 4.9 mg/kg for 70 kg patients), it may be administered once or even twice a week for 4 to 10 weeks. Alternatively, the time course of administration can be reduced, i.e., once every 2 or 3 weeks for 2-3 months. However, it has been determined that even higher doses can be administered by slow i.v. infusion, such as 20 mg/kg once a week or once every 2-3 weeks, for repeated dosing cycles. The time course of administration can optionally be repeated at other intervals, and the dosage can be administered by various parenteral routes with appropriate adjustments in dosage and time course.

In a preferred embodiment, the conjugate or pharmaceutical composition described herein is useful in the treatment of cancer therapy. Examples of cancer include, but are not limited to, carcinoma, lymphoma, glioblastoma, melanoma, sarcoma and leukemia, myeloma or lymphoid malignancy. More specific examples of the cancer are described below and include: squamous cell carcinoma (e.g., epithelial squamous cell carcinoma), Ewing's sarcoma, Wilms' tumor, astrocytoma, lung cancer (including small cell lung cancer, non-small cell lung cancer, lung adenocarcinoma and lung squamous cell carcinoma), peritoneal cancer, hepatocellular cancer, gastric cancer or stomach cancer (including gastrointestinal cancer), pancreatic cancer, glioblastoma multiforme, cervical cancer, ovary cancer, liver cancer, bladder cancer, hepatocellular cancer, hepatocellular carcinoma, neuroendocrine tumor, medullary thyroid carcinoma, thyroid differentiation cancer, breast cancer, ovarian cancer, colon cancer, rectal cancer, endometrial cancer or uterine cancer, salivary gland cancer, renal or kidney cancer, prostate cancer, vulva cancer, anal cancer, penile cancer, and head and neck cancer. The term "cancer" includes primary malignant cell or tumor (e.g., a tumor where cells have not migrated to a site in a subject other than the original malignant disease or tumor site) and secondary malignant cells or tumors (e.g., a tumor produced by metastasis, i.e., malignant cells or tumor cells migrating to a secondary site different from the original tumor site). Cancers that benefit from the therapeutic method of the invention are directed to cells that express, overexpress, or aberrantly express IGF-IR.

Other examples of the cancer or malignant disease include, but are not limited to, acute childhood lymphoblastic leukemia, acute lymphoblastic leukemia, acute lymphocytic leukemia, acute myeloid leukemia, adrenocortical carcinoma, adult (primary) hepatocellular carcinoma, adult (primary) liver cancer, adult acute lymphocytic leukemia, adult acute myeloid leukemia, adult Hodgkin's lymphoma, adult lymphocytic lymphoma, adult non-Hodgkin's lymphoma, adult primary liver cancer, adult soft tissue sarcoma, AIDS-related lymphoma, AIDS-related malignant disease, anal cancer, astrocytoma, cholangiocarcinoma, bladder cancer, bone cancer, brain stem glioma, brain tumor, breast cancer, renal pelvis and ureteral cancer, central nervous system (primary) lymphoma, central nervous system lymphoma, cerebellar astrocytoma, cerebral astrocytoma, cervical cancer, children (primary) hepatocellular carcinoma, children (primary) liver cancer, children acute lymphoblastic leukemia, children acute myeloid leukemia, children brain stem glioma, children cerebellar astrocytoma, children cerebral astrocytoma, children extracranial blastoma, Hodgkin's disease in children, Hodgkin's lymphoma in children, hypothalamic and visual pathway glioma in children, lymphoblastic leukemia in children, medulloblastoma in children, non-Hodgkin's lymphoma in children, pineal gland and supratentorial primitive neuroectodermal tumor in children, children primary liver cancer, childhood rhabdomyosarcoma, childhood soft tissue sarcoma, childhood visual pathway and hypothalamic glioma, chronic lymphocytic leukemia, chronic myeloid leukemia, colon cancer, cutaneous T-cell lymphoma, endocrine islet cell carcinoma, endometrial cancer, ependymoma, epithelial cancer, esophageal cancer, Ewing's sarcoma and related tumors, exocrine pancreatic cancer, extracranial blastoma, extragonadal blastoma, extrahepatic cholangiocarcinoma, eye cancer, female breast cancer, Gaucher's disease, gallbladder cancer, stomach cancer, benign gastrointestinal tumor, gastrointestinal tumor, blastocytoma, gestational trophoblastic cell tumor, hairy cell leukemia, head and neck cancer, hepatocellular carcinoma, Hodgkin's lymphoma, hypergammaglobulinemia, hypopharyngeal carcinoma, intestinal cancer, intraocular melanoma, islet cell carcinoma, islet cell pancreatic cancer, Kaposi's sarcoma, kidney cancer, laryngeal cancer, lip and mouth cancer, liver cancer, lung cancer, lymphoproliferative disorders, macroglobulinemia, male breast cancer, malignant mesothelioma, malignant thymoma, medulloblastoma, melanoma, mesothelioma, metastatic primary occult squamous neck cancer, metastatic primary squamous neck cancer, metastatic squamous neck cancer, multiple myeloma, multiple myeloma/plasma neoplasms, myelodysplastic syndrome, myeloid leukemia, myelogenous leukemia, myeloproliferative disorders, nasal and paranasal sinus cancer, nasopharyngeal carcinoma, neuroblastoma, non-Hodgkin's lymphoma, non-melanoma skin cancer, non-small cell lung cancer, metastatic primary occult squamous neck cancer, oropharyngeal cancer, osteosarcoma/malignant fibrosarcoma, osteosarcoma/malignant fibrous histiocytoma, osteosarcoma/malignant fibrous histiocytoma in bone, ovarian epithelial carcinoma, ovarian blastoma, ovarian low malignant potential tumor, pancreatic cancer, diseased proteinemia, polycythemia vera, parathyroid carcinoma, penile cancer, pheochromocytoma, pituitary tumor, primary central nervous system lymphoma, primary liver cancer, prostate cancer, rectal cancer, renal cell carcinoma, renal pelvis and ureteral cancer, retinoblastoma, rhabdomyosarcoma, salivary gland cancer, sarcoidosis sarcoma, Sezary syndrome, skin cancer, small cell lung cancer, small bowel cancer, soft tissue sarcoma, squamous neck cancer, gastric cancer, supratentorial primitive neuroectodermal and pineal tumor, T cell lymphoma, testicular cancer, thymoma, thyroid cancer, renal pelvis and ureteral transitional cell carcinoma, transitional renal pelvis and ureteral cancer, trophoblastic tumor, ureter and renal pelvic cell carcinoma, ureteral cancer, uterine cancer, uterine sarcoma, vaginal cancer, visual pathway and hypothalamic glioma, vulva cancer, Waldenstrom's macroglobulinemia, Wilms' tumor, and any other hyperproliferative disease other than a neoplasma located in the organ system listed above.

The conjugate, composition, and method described and claimed herein can be used to treat malignant or pre-malignant condition and to prevent progression to a neoplastic or malignant state, including but not limited to those described above. It is indicated that such use is related to conditions that are known or suspected to progress in advance into a neoplasma or cancer, especially in the case of non-neoplastic cell growth that has occurred from hyperplasia, metaplasia or, most particularly, dysplasia. For a review of such abnormal growth conditions, see Robbins and Angell, BASIC PATHOLOGY, 2nd ed., W.B. Saunders Co., Philadelphia, pp. 68-79 (1976).

Dysplasia is often a precursor to cancer and is primarily found in the epithelium. It is the most disordered form of non-neoplastic cell growth and involves the loss of individual cell consistency and cell structure orientation. In the presence of chronic irritation or inflammation, dysplasia characteristically occurs. Dysplastic disorders that can be treated include, but are not limited to, non-perspiring ectodermal dysplasia, anterior dysplasia, asphyxiating thoracic dysplasia, atrial-finger dysplasia, bronchopulmonary dysplasia, cerebral dysplasia, cervical dysplasia, cartilage ectodermal dysplasia, clavicular skull dysplasia, congenital ectodermal dysplasia, skull diaphysis dysplasia, cranium carpus tarus dysplasia, skull metaphyseal dysplasia, dentine dysplasia, diaphysis dysplasia, ectodermal dysplasia, dental enamel dysplasia, cerebral eyeball dysplasia, lateral epiphyseal dysplasia, multiple epiphyseal dysplasia, punctate epiphyseal dysplasia, epithelial dysplasia, facial phalangeal genital dysplasia, familial jaw fibrous dysplasia, familial white wrinkle dysplasia, fibromuscular dysplasia, bone fibrous dysplasia, vigorous bone dysplasia, hereditary renal retinal dysplasia, perspiring ectodermal dysplasia, hypohidrotic ectodermal dysplasia, lymphopenia thymic dysplasia, mammary gland dysplasia, mandibular face dysplasia, metaphyseal dysplasia, Montini's dysplasia, monofibrillar bone dysplasia, mucous epithelial dysplasia, multiple epiphyseal dysplasia, ocular aural vertebral dysplasia, ocular dental phalangeal dysplasia, ocular vertebral dysplasia, odontogenic dysplasia, ocular mandibular dysplasia, root tip periodontal cemental dysplasia, multifibrous bone dysplasia, pseudoachondroplasia vertebral epiphyseal dysplasia, retinal dysplasia, septal-ocular dysplasia, vertebral epiphyseal dysplasia and Cerebroventricular radial dysplasia.

Other pre-neoplastic disorders that can be treated include, but are not limited to, benign abnormal proliferative disorders (e.g., benign tumors, fibrocystic conditions, tissue hypertrophy, intestinal polyps or adenomas and esophageal dysplasia), leukoplakia, keratosis, Bowen's Disease, farmer's skin, solar cheilitis and solar keratosis.

In a preferred embodiment, the method of the invention is used to inhibit cancers, particularly the growth, progression and/or metastasis of the cancers listed above.

Other hyperproliferative diseases, disorders, and/or conditions include, but are not limited to, progression and/or metastasis of malignant diseases and related conditions, such as leukemia (including acute leukemia (e.g., acute lymphocytic leukemia, acute myeloid leukemia (including myeloblastic, promyelocytic, myelomonocytic, monocytic, and erythroleukemia)) and chronic leukemia (e.g., chronic myeloid (granulocytic) leukemia and chronic lymphocytic leukemia)), polycythemia vera, lymphoma (e.g., Hodgkin's disease and non-Hodgkin's disease), multiple myeloma, Waldenstrom's macroglobulinemia, heavy chain disease, and solid tumors, including but not limited to sarcoma and carcinoma, such as fibrosarcoma, mucinous sarcoma, liposarcoma, chondrosarcoma, osteosarcoma, chordoma, angiosarcoma, endothelial sarcoma, lymphangiosarcoma, lymphatic endothelial sarcoma, synovial tumor, mesothelioma, Ewing's Tumor, leiomyosarcoma, rhabdomyosarcoma, colon cancer, pancreatic cancer, breast cancer, ovarian cancer, prostate cancer, squamous cell carcinoma, basal cell carcinoma, adenocarcinoma, sweat gland cancer, sebaceous gland cancer, papillary carcinoma, papillary adenocarcinoma, cystadenocarcinoma, medullary carcinoma, bronchial carcinoma, renal cell carcinoma, hepatoma, cholangiocarcinoma, choriocarcinoma, seminoma, embryonal cancer, Wilms' tumor, cervical cancer, testicular cancer, lung cancer, small cell lung cancer, bladder cancer, epithelial cancer, glioma, astrocytoma, medulloblastoma, craniopharyngioma, ependymoma, pineal gland tumor, hemangioblastoma, acoustic neuroma, oligodendroglioma, meningioma, melanoma, neuroblastoma and retinoblastoma.

Kit

Various embodiments may involve a kit containing a component suitable for treating or diagnosing diseased tissue of a patient. An exemplary kit can contain one or more conjugates, leukocytes, and/or other therapeutic agents as described herein. If a composition containing multiple components for administration is not formulated for delivery via the digestive tract, such as by oral delivery, a device capable of delivering the components of the kit by some other routes may be included. One type of device for applications such as parenteral delivery is a syringe for injecting a composition into a subject. An inhalation device can also be used. In certain embodiments, the therapeutic agent can be provided in the form of a prefilled syringe or autoinjector pen containing a sterile liquid formulation or a lyophilized formulation.

The components of kit can be packaged together or separated into two or more containers. In some embodiments, the container can be a vial containing a sterile lyophilized formulation of a composition suitable for reconstitution. The kit may also contain one or more buffers suitable for reconstitution and/or dilution of other reagents. Other containers that may be used include, but are not limited to, bags, trays, boxes, tubes, and the like. The components of kit can be aseptically packaged and maintained in a container. Another component that can be included is the insert or leaflet for the kit.

EXAMPLE

The following examples are provided to illustrate the invention but not to limit the claims of the invention.

Example 1. Preparing Bispecific Binding Conjugate Anti-CD56-PLGA-anti-CD20

A bispecific binding conjugate anti-CD56-PLGA-anti-CD20 having an anti-CD56 antibody and an anti-CD20 antibody coupled to different nanoparticles (PLGA, PLA and PCL) was prepared.

The specific method for preparing the bispecific binding conjugate anti-CD56-PLGA-anti-CD20 is as follows:

(1) preparing a PLGA nanoparticle: completely dissolving the PLGA in acetone at a concentration of 5 mg/mL, and adding the solution of PLGA in acetone into deionized water in a volume ratio of 1:4 of acetone and deionized water with magnetic stirring at 1000 rpm/min, to form a uniform emulsion, and then continuing to stir until volatilization of acetone;

(2) collecting the PLGA nanoparticle: collecting the prepared nanoparticle with larger particle size by centrifugation at 8000 rpm/min for 10 min; then collecting the prepared nanoparticle with smaller particle size by centrifugation at 15000 rpm/min for 10 min, discarding the nanoparticle with larger particle size and resuspending the nanoparticle with smaller particle size in deionized water, and repeating the process twice to wash the nanoparticle. The nanoparticle with smaller particle size is used in the process as follows;

(3) activating the PLGA nanoparticle: using a mixed solvent of 5 mg/mL 1-ethyl-(3-dimethyl aminopropyl)carbodiimide hydrochloride and N-hydroxysuccinimide at room temperature to activate the PLGA nanoparticle for 1 h;

(4) connecting the PLGA nanoparticle to antibodies: collecting the activated nanomaterial by centrifugation, and then washing the nanomaterial once with 0.1 M D-PBS at pH=8.0, mixing the anti-CD56 monoclonal antibody (mAb) and the anti-CD20 mAb (both monoclonal antibodies are purchased from Tong Li Hai Yuan Biological Company) to be ligated in an equal amount and adding them to the ligation reaction solution, then resuspending the nanomaterial with the connecting reaction solution containing the anti-CD56 mAb and the anti-CD20 mAb, and conducting the connecting reaction for 0.5 h at room temperature. After the reaction, the nanomaterial is collected by centrifugation. The nanomaterial is washed twice in D-PBS, and then resuspended in D-PBS and stored at 4° C.

The specific method for preparing the bispecific binding conjugate anti-CD56-PLA-anti-CD20 is as follows:

(1) preparing a PLA nanoparticle: completely dissolving PLA in methanol at a concentration of 15 mg/mL, adding the solution of PLA in methanol into deionized water in a volume ratio of 1:4 of methanol and deionized water with magnetic stirring at 500 rpm/min, to form a uniform emulsion, and then continuing to stir until volatilization of methanol;

(2) collecting the PLA nanoparticle: collecting the prepared nanoparticle by centrifugation at 10000 rpm/min for 10 min, and then resuspending the nanoparticle in deionized water, and repeating the process twice to wash the nanoparticle;

(3) activating the PLA nanoparticle: using a mixed solvent of 1 mg/mL 1-ethyl-(3-dimethyl aminopropyl)carbodiimide hydrochloride and N-hydroxysuccinimide at room temperature to activate the PLA nanoparticles for 0.5 h (4) connecting the PLA nanoparticle to antibodies: collecting the activated nanomaterial by centrifugation, then washing the nanomaterial once with 0.1 M D-PBS at pH=8.0, mixing the anti-CD56 mAb and the anti-CD20 mAb to be ligated in an equal amount and adding them to the ligation reaction solution, resuspending the nanomaterial with the connecting reaction solution containing the anti-CD56 mAb and the anti-CD20 mAb, and conducting the connecting reaction for 0.5 h at room temperature. After the reaction, the nanomaterial is collected by centrifugation and washed twice in D-PBS, and then resuspended in D-PBS and stored at 4° C.

The specific method for preparing the bispecific binding conjugate anti-CD56-PCL-anti-CD20 is as follows:

(1) preparing a PCL nanoparticle: completely dissolving PCL in isopropyl alcohol at a concentration of 30 mg/mL, adding the solution of PCL in isopropyl alcohol into deionized water in a volume ratio of 1:4 of isopropyl alcohol and deionized water with magnetic stirring at 1500 rpm/min, to form a uniform emulsion, and then continuing to stir until volatilization of isopropyl alcohol;

(2) collecting the PCL nanoparticle: collecting the prepared nanoparticle by centrifugation at 15000 rpm/min, and then resuspending the nanoparticle in deionized water, which processes are repeated twice to wash the nanoparticle;

(3) activating the PCL nanoparticle: using a mixed solvent of 10 mg/mL 1-ethyl-(3-dimethylaminopropyl)carbodiimide hydrochloride and N-hydroxysuccinimide at room temperature to activate the PCL nanoparticle for 2 h;

(4) connecting the PCL nanoparticle to antibodies: collecting the activated nanomaterial by centrifugation, then washing the nanomaterial once with 0.1 M D-PBS at pH=8.0, mixing the anti-CD56 mAb and the anti-CD20 mAb to be ligated in an equal amount and adding them to the ligation reaction solution, resuspending the nanomaterial with the connecting reaction solution containing the anti-CD56 mAb and the anti-CD20 mAb, and conducting the connecting reaction for 3 h at room temperature. After the reaction, the nanomaterial is collected by centrifugation and washed twice in D-PBS, and then resuspended in D-PBS and stored at 4° C.

Example 2. Preparing Other Bispecific Binding Conjugates

Other bispecific binding conjugates i.e. anti-CD16-PLGA-anti-MUC1, anti-CD56-PLGA-anti-MUC1, anti-CD16-PLGA-anti-CD19, anti-CD56-PLGA-anti-CD19, anti-CD16-PLGA-anti-CD20 and anti-CD56-PLGA-anti-CD20 were prepared in a manner similar to that described in Example 1. The antibodies used therein are all commercially available monoclonal antibodies.

In addition, anti-CD56-PLA-anti-CD19, anti-CD56-PCL-anti-CD19, anti-CD16-PLA-anti-CD20, anti-CD16-PCL-anti-CD20, anti-CD16-PLA-anti-MUC1 and anti-CD16-PCL-anti-MUC1 were also prepared in a manner similar to that described in Example 1.

Example 3. Efficacy of Bispecific Binding Conjugates on Killing Cancer Cells The ability of the bispecific binding conjugates prepared in Example 1 and Example 2 to kill tumor cells was evaluated.

Specifically, 5000 target cells per well were cultured for 12 h in 96-well plates and then the initial medium was discarded. The cytokine-free X-vivo 15 medium (purchased from lonza) was used to adjust the density of NK cells (induced by peripheral blood mononuclear cells from healthy blood donors), so that number of NK cells in a volume of 100 μl reaches 4 times larger than that of the target cells (effector to target ratio is 4:1). 100 μl suspension of NK cells was added in a cancer cell culture plate, and 10 μl prepared bispecific binding conjugate (bispecific binding conjugate content: 0.2 mg, with a total amount of monoclonal antibodies 0.2 μg) was added, incubated for 8 h in an incubator, and then CCK-8 reagent was added, incubated according to the reagent instruction. The absorbance at 450 nm was measured using a microplate reader. Statistical analysis of the data was performed, according to the following formula to calculate killing rate of DC-CIK cells on cancer cells.

Killing rate=[1−(experimental group−effector control group)/(target control group−blank control group)]×100%

The blank control group represents the added medium; the target control group represents the added target cell+medium; the effector control group represents the added effector cell+medium; the experimental group represents the effector cell+target cell+medium+bispecific binding conjugate.

The results are shown in Tables 1-2 and FIGS. 2-7.

TABLE 1

Ability of bispecific binding conjugates to kill tumor cells (effector-target ratio of 4:1)

| Cancer cell | Effector control group (NK) | Killing rate Experimental group (NK + conjugate) | |
|---|---|---|---|
| | | Anti-CD56-PLGA-anti-CD20 | Anti-CD16-PLGA-anti-MUC1 |
| HKC | 7.44% | 9.23% | 11.23% |
| A549 | 9.58% | 81.91% | 89.91% |
| HepG2 | 14.68% | 89.36% | 80.36% |
| HT29 | 15.67% | 92.47% | 82.47% |
| MCF-7 | 19.57% | 77.23% | 87.23% |
| AGS | 12.46% | 93.21% | 84.21% |
| Hela | 15.76% | 79.64% | 85.64% |
| 5637 | 13.57% | 80.74% | 87.74% |
| OS-RC-2 | 10.62% | 94.47% | 80.47% |

Note:
HKC—human embryo kidney epithelial cells; A549—human non-small cell lung cancer cells; HepG2—human liver cancer cells; HT29—human colon cancer cells; AGS—human gastric adenocarcinoma cells; Hela—human cervical cancer cells; 5637—human bladder cancer cells; OS-RC-2—human kidney cancer cells.

TABLE 2

Ability of bispecific binding conjugates to kill tumor cells (effector-target ratio of 4:1)

| Cancer cell | Effector control group (NK) | Killing rate Experimental group (NK + conjugate) | | | |
|---|---|---|---|---|---|
| | | Anti-CD16-PLGA-anti-CD19 | Anti-CD56-PLGA-anti-CD19 | Anti-CD16-PLGA-anti-CD20 | Anti-CD56-PLGA-anti-CD20 |
| Raji | 12.59% | 79.91% | 83.85% | 91.54% | 92.94% |
| RAMOS | 17.67% | 81.36% | 90.27% | 94.38% | 85.37% |

Note:
Raji—black Burkitt lymphoma cells; RAMOS—human B lymphocytoma cells. Anti-CD56-PLA-anti-CD19 and anti-CD56-PCL-anti-CD19 showed a killing rate greater than 83% for black Burkitt lymphoma cells and human B lymphocytoma cells (specific data not shown).
Anti-CD16-PLA-anti-CD20 and anti-CD16-PCL-anti-CD20 showed a killing rate greater than 83% for black Burkitt lymphoma cells and human B lymphocytoma cells (specific data not shown).
Anti-CD16-PLA-anti-MUC1 and anti-CD16-PCL-anti-MUC1 showed a killing rate greater than 95% for human non-small cell lung cancer cells; greater than 92% for human bladder cancer cells and human breast cancer cells; nearly 85% for human cervical cancer cells and human gastric adenocarcinoma cells; greater than 80% for human colon cancer cells, human kidney cancer cells and human liver cancer cells.

Example 4. Experiment of Inhibiting Tumor In Vitro

Anti-CD3 and/or anti-CD16 and anti-MUC1 bispecific or trispecific binding conjugates connected by PLGA (i.e. anti-CD3-PLGA-anti-MUC1, anti-CD16-PLGA-anti-MUC1 or anti-CD3 plus anti-CD16-PLGA-anti-MUC1, hereinafter referred to as CD3-MUC1 group, CD16-MUC1 group and CD3/CD16-MUC1 group, respectively) were prepared according to the methods of the previous Examples, wherein the antibodies used were all commercially available.

Figure 8:
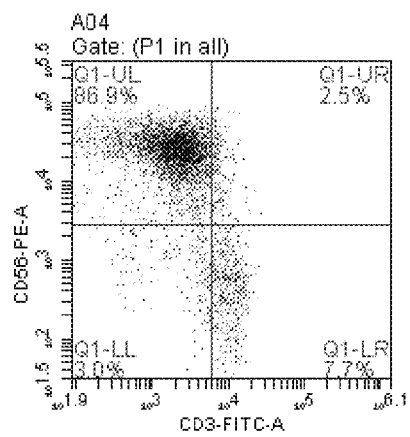
FIG. 8 shows the ratio of NK (CD3-CD56+) cells and CD3+ T cells in the prepared effector cells.

The ability of the bispecific or trispecific binding conjugates to assist NK to kill A549 cells was evaluated. Specifically, 50 ml of peripheral blood of healthy human was collected, monocytes (PBMC) were isolated, and then NK cytokines were added for induction and expansion culture. The percentage of NK cells was measured by culturing cells until day 21. The results were as follows: the ratio of NK cells was 86.9%, and the ratio of CD3+ T cells was 10.2% (see FIG. 8). 5000 A549 cells as target cells were cultured in each well for 12 h in 96-well plates and then the initial medium was discarded. The cytokine-free X-vivo 15 medium was used to adjust the density of NK cells, so that the number of NK cells in a volume of 100 μl was 4 times larger than that of the target cells (effector-target ratio is 4:1). 100 μl suspension of NK cells was added in a cancer cell culture plate, and 10 μl prepared bispecific binding conjugates (the content of bispecific binding conjugate was 0.2 mg, with a total amount of monoclonal antibodies 0.2 μg) were added, incubated for 8 h in an incubator, and then CCK-8 reagent added, incubated according to the reagent instructions. The absorbance at 450 nm was measured using a microplate reader. Statistical analysis of the data was performed, according to the following formula to calculate killing rate of NK cells on cancer cells.

Killing rate=[1−(experimental group−effector control group)/(target control group−blank control group)]×100%

Figure 9:
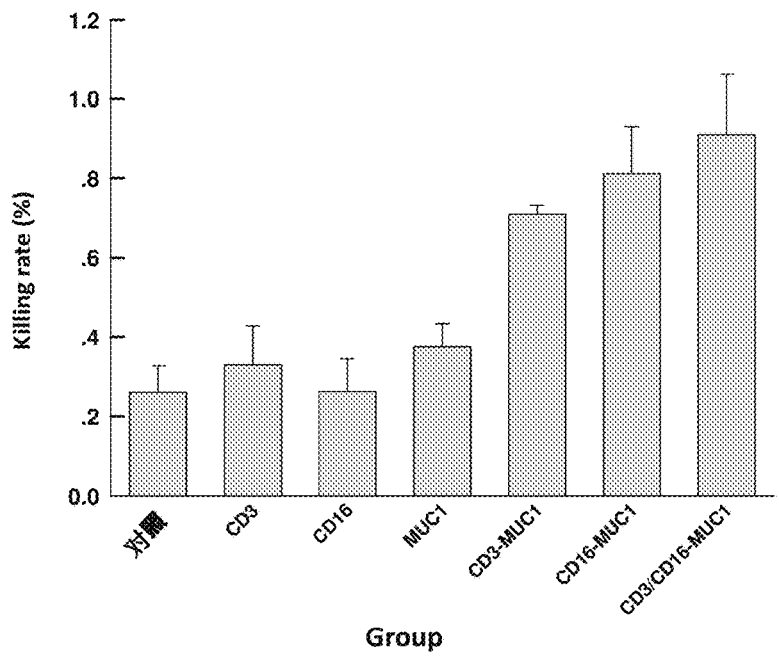
FIG. 9 shows the ability of the bispecific or trispecific binding conjugate to aid NK in killing cancer cells.

The results of the experiment showed (see FIG. 9): NK, CD3 monoclonal antibody+NK, CD16 monoclonal antibody+NK, MUC1 monoclonal antibody+NK showed a certain effect, and the statistical results showed that compared with the control group, the tumor inhibition rates were 26.1%, 33.02%, 26.22%, and 37.51%, respectively, and there was no significant difference between the groups. The tumor inhibition rates of CD3-MUC1, CD16-MUC1, CD3/CD16-MUC1 groups to assist NK cells were 71.02%, 81.84%, and 90.91%, respectively, which showed good efficacy, with CD3/CD16-MUC1>CD16-MUC1>CD3-MUC1 and also closely related to the cellular components in NK cells. NK generally expresses CD16, and the proportion of NK cells is much larger than that of CD3+ T cells. Therefore, it is appropriate to use CD16 as the recognition site of NK. Because the NK cell population currently induced in vitro has NK cells at a ratio of about 86.9% and some other effector cells (including 10.2% of CD3+ T cells), the anti-tumor effect of CD16 and CD3 both of which are connected is better.

Example 5. Experiment of Inhibiting Tumor In Vivo

The anti-tumor efficacy of the bispecific or trispecific binding conjugates described in Example 4 was evaluated in vivo. Specifically, healthy Balb-c nude mice (clean grade, female, four weeks old, body weight 18-22 g, purchased from Beijing Vital Lihua Experimental Animal Technology Co., Ltd.) were inoculated with human lung adenocarcinoma cell A549 were at oxter. After 3-4 weeks of inoculation, 90 nude mice with a tumor diameter of about 0.5×0.5 cm were randomly divided into 8 groups for experiments (grouping is shown below).

| Groups | Experimental treatments |
|---|---|
| Control | normal saline 100 ul |
| NK | 1 × 10$^6$ NK cells |
| CD | 1 × 10$^6$ NK cells + CD3 mAb |
| CD16 | 1 × 10$^6$ NK cells + CD16 mAb |
| MUC1 | 1 × 10$^6$ NK cells + MUC1 mAb |
| CD3-PLGA-MUC1 | 1 × 10$^6$ NK cells + CD3-PLGA-MUC1 bispecific binding conjugate |
| CD16-PLGA-MUC1 | 1 × 10$^6$ NK cells + CD16-PLGA-MUC1 bispecific binding conjugate |
| CDS/CD16-PLGA-MUC1 | 1 × 10$^6$ NK cells + CD3/CD16-PLGA-MUC1 trispecific binding conjugate |

The mice were administered by tail vein injection on days 1, 2, and 3, respectively. Each experimental group was injected with 20 μl of antibody or binding conjugate preparation each time, wherein the preparation contained 12.5 μg of each monoclonal antibody, that is, 0.25 μg of antibody per animal was injected in the monoclonal antibody group, 0.50 μg of antibody per animal in total was injected in the bispecific binding conjugate group, and 0.75 μg of antibody per animal in total was injected in the trispecific binding conjugate group. The control group was injected with the same volume of normal saline.

The volume of the recorded tumor was measured from the first day. The therapeutic effect of the bispecific/trispecific binding conjugates on the tumor was calculated.

Figure 10:
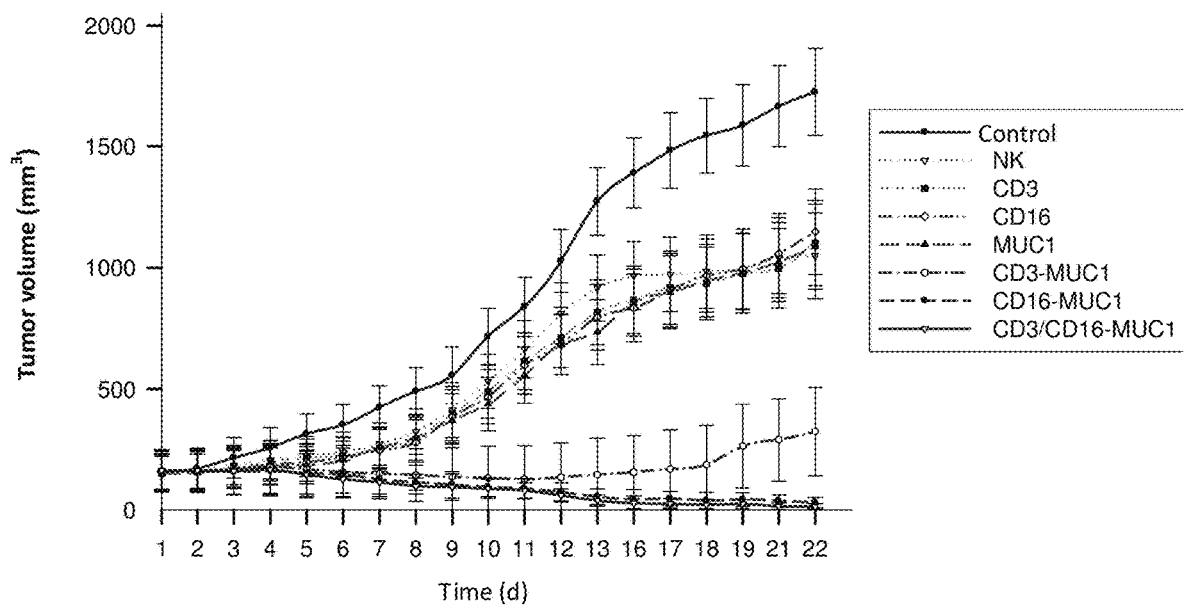
FIG. 10 shows the efficacy of the prepared bispecific or trispecific binding conjugate on inhibiting tumors in vivo.

FIG. 10 shows the statistical changes in tumor volume. The results of the first 22 days of the experiment showed that: NK, CD3 monoclonal antibody+NK, CD16 monoclonal antibody+NK, MUC1 monoclonal antibody+NK showed a certain effect, and the current statistical results showed that compared with the control group, the tumor inhibition rate was 39.24%, 36.19%, 33.49%, and 37.01%, respectively, and there was no significant difference among the groups. The tumor inhibition rates of CD3-MUC1, CD16-MUC1, CD3/CD16-MUC1 to assist NK cells were 81.22%, 88.24%, and 95.15%, respectively, which showed good efficacy, with CD3/CD16-MUC1>CD16-MUC1>CD3-MUC1 and also closely related to the cellular components in NK cells. NK generally expresses CD16, and the proportion of NK cells is much larger than that of CD3+ T cells. Therefore, it is appropriate to use CD16 as the recognition site of NK. Because the NK cell population currently induced in vitro has NK cells at a ratio of about 86.9% and some other effector cells (including 10.2% of CD3+ T cells), the anti-tumor effect of CD16 and CD3 both of which are connected is better.

In accordance with the present disclosure, all of the conjugates, compositions, and methods disclosed and claimed herein can be made and used without undue experimentation. Although the compositions and methods have been described in terms of the preferred embodiments, it will be apparent to those skilled in the art that the conjugates, compositions and methods described herein as well as the steps or step sequences in the methods can vary without departing from the concept, spirit and scope of the invention. More specifically, certain reagents that are chemically and physiologically related may be substituted for the reagents described herein while achieving the same or similar results. All such similar substitutions and modifications which are obvious to those skilled in the art, are within the spirit, scope and concept of the invention as defined by the appended claims.

What is claimed is:

1. A multispecific binding conjugate comprising:
   a) at least one first binding moiety that binds an antigen on an NK cell; and
   b) at least one second binding moiety that binds to an antigen on a target cell
   wherein each of the first binding moiety and the second binding moiety is selected from the group consisting of an antibody or an antigen-binding fragment thereof;
   wherein the first binding moiety and the second binding moiety are coupled to a biodegradable nanomaterial which is poly(lactic acid-co-glycolic acid); and
   wherein the target cell is a tumor cell, the antigen on the target cell is Muc1, and the antigen on the NK cell is CD16.

2. A pharmaceutical composition comprising the conjugate of claim 1.

3. The pharmaceutical composition according to claim 2 further comprising leukocyte, wherein the leukocyte comprises an NK cell.

4. The pharmaceutical composition according to claim 2, further comprising an additional therapeutic agent selected from the group consisting of an antibody antibody fragment, a drug, a toxin, an enzyme, a cytotoxic agent, an anti-angiogenic agent, proapoptotic agent, antibiotic, hormone, immunomodulator, cytokine, chemokine, antisense oligonucleotide, small interfering RNA (siRNA), boron compound, and radioisotope.

5. A method of treating a cancer in a subject in need thereof, comprising administering to the subject a multispecific binding conjugate according to claim 1.

6. The method according to claim 5, wherein the cancer is selected from the group consisting of non-Hodgkin's lymphoma, B cell lymphoma, B cell leukemia, T cell lymphoma, T cell leukemia, acute lymphocytic leukemia, chronic lymphocytic leukemia, Burkitt's lymphoma, Hodgkin's lymphoma, hairy cell leukemia, acute myelogenous leukemia, chronic myelogenous leukemia, multiple myeloma, glioma, Waldenstrom's macroglobulinemia, carcinoma, melanoma, sarcoma, glioma, skin cancer, oral cancer, gastrointestinal cancer, colon cancer, stomach cancer, lung cancer, breast cancer, ovarian cancer, prostate cancer, uterine cancer, endometrial cancer, cervical cancer, bladder cancer, pancreatic cancer, bone cancer, liver cancer, gallbladder cancer, kidney cancer, testicular cancer, epithelial cancer, colorectal cancer, stomach cancer, brain cancer, glioblastoma, pancreatic cancer, myeloid leukemia, cervical cancer, medullary thyroid carcinoma, astrocytoma, prostate cancer, bladder cancer, neuroendocrine cancer, gastrointestinal pancreatic tumor, exocrine pancreatic cancer and Ewing sarcoma.

7. The method according to claim 5, further comprising administering to the subject an additional therapeutic agent selected from the group consisting of an antibody, an antibody fragment, a drug, a toxin, an enzyme, a cytotoxic agent, an anti-angiogenic agent, pro-apoptotic agent, antibiotic, hormone, immunomodulator, cytokine, chemokine, anti sense oligonucleotide, small interfering RNA (siRNA), boron compound, and radioisotope.

8. A method of treating a cancer in a subject in need thereof, comprising administering to the subject a pharmaceutical composition according to claim 2.

9. The method according to claim 8, wherein the cancer is selected from the group consisting of non-Hodgkin's lymphoma, B cell lymphoma, B cell leukemia, T cell lymphoma, T cell leukemia, acute lymphocytic leukemia, chronic lymphocytic leukemia, Burkitt's lymphoma, Hodgkin's lymphoma, hairy cell leukemia, acute myelogenous leukemia, chronic myelogenous leukemia, multiple myeloma, glioma, Waldenstrom's macroglobulinemia, carcinoma, melanoma, sarcoma, glioma, skin cancer, oral cancer, gastrointestinal cancer, colon cancer, stomach cancer, lung cancer, breast cancer, ovarian cancer, prostate cancer, uterine cancer, endometrial cancer, cervical cancer, bladder cancer, pancreatic cancer, bone cancer, liver cancer, gallbladder cancer, kidney cancer, testicular cancer, epithelial cancer, colorectal cancer, stomach cancer, brain cancer, glioblastoma, pancreatic cancer, myeloid leukemia, cervical cancer, medullary thyroid carcinoma, astrocytoma, prostate cancer, bladder cancer, neuroendocrine cancer, gastrointestinal pancreatic tumor, exocrine pancreatic cancer and Ewing sarcoma.

* * * * *